US006355422B1

(12) United States Patent
Liu et al.

(10) Patent No.: US 6,355,422 B1
(45) Date of Patent: Mar. 12, 2002

(54) SINGLE TUBE PCR ASSAY FOR DETECTION OF CHROMOSOMAL MUTATIONS: APPLICATION TO THE INVERSION HOTSPOT IN THE FACTOR VIII GENE INCLUDING OPTIONAL USE OF SUBCYCLING PCR

(75) Inventors: Qiang Liu, Arcadia; Steve S. Sommer, Duarte, both of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/200,934

(22) Filed: Nov. 30, 1998

Related U.S. Application Data

(63) Continuation-in-part of application No. 09/103,505, filed on Jun. 24, 1998.
(60) Provisional application No. 60/113,669, filed on Jun. 24, 1998.

(51) Int. Cl.[7] .................................................. C12Q 1/68
(52) U.S. Cl. ........................ 435/6; 435/91.1; 435/91.2; 435/7.1; 435/7.2; 536/23.1; 536/24.3; 536/24.31; 536/24.32
(58) Field of Search .......................... 435/6, 91.1, 91.2, 435/7.2, 7.1; 536/23.1, 24.3, 24.31, 24.32

(56) References Cited

U.S. PATENT DOCUMENTS 5,552,283 A * 9/1996 Diamandis et al. ............. 435/6
5,928,905 A * 7/1999 Stemmer et al. ........... 435/91.1

OTHER PUBLICATIONS

Antonarakis, S.E. (1995), "Molecular Genetics of Coagulation Factor VIII Gene and Hemophilia A", *Thromb. Haemost.*, vol. 74(1):322–328.
Antonarakis, S.E. (1995), et al., "Factor VIII Gene Inversions in Severe Hemophilia A: Results of an International Consortium Study", *Blood*, 86(6):2206–2212.
Antonarakis, S.E., et al. (1995), "Molecular Etiology of Factor VIII Deficiency in Hemophilia A", *Hum. Mutat.*, 5(1):1–22.
Barnes, W.M. (1994), "PCR amplification of up to 35–kb DNA with high fidelity and high yield from λ bacteriophage templates", *Proc. Natl. Acad. Sci. USA*, 91:2216–2220.
Baskaran, N. (1996), et al., "Uniform Amplification of a Mixture of Deoxyribonucleic Acids with Varying GC Content", *Genome Research*, 6:633–638.
Bowen, D.J. and Davies, S.V. (1995), "Factor VIII Gene Rearrangements in Severe Hemophilia A", *Blood*, 85(1):291.
Chamberlain, J.S., et al. (1988), "Deletion screening of the Duchenne muscular dystrophy locus via multiplex DNA amplification", *Nucleic Acids Research*, 16(23):11141–11156.

Cheng, S., et al. (1994), "Effective amplification of long targets from cloned inserts and human genomic DNA", *Proc. Natl. Acad. Sci. USA*, 91:5695–5699.
Day, I.N. (1997), "Molecular biology series 5 Polymerase chain reaction", *Br. J. Hosp. Med.*, 57(4):170–171.
Fujimura, F.K., et al., "Carrier Detection for Hemophilias A and B Using Direct Mutation Scanning Methods", XXIII International Congress of the World Federation of Hemophilia. The Hague, The Netherlands, May 17–21, 1998. Abstract #16–28.
Gitschier, J. and Wood, W.I. (1992), "Sequence of the exon–containing regions of the human factor VIII gene", *Hum. Mol. Genet.*, 1(3):199–200.
Henegariu, O., et al. (1997), "Multiplex PCR: Critical Parameters and Step–by–Step Protocol", *Bio Techniques*, 23(3):504–511.
Ishak, R. and Khim, L.C. (1996), "Amplification of Bcl I Region of the Factor VIII Gene by PCR", *Southeast Asian J. Trop. Med. Public Health*, 27(2):364–366.
Lakich, D., et al. (1993), "Inversions disrupting the factor VIII gene are a common cause of severe haemophilia A", *Nature Genet.*, 5:236–241.
Liu, Q., et al. (1996), "Bi–directional dideoxy fingerprinting (Bi–ddF): a rapid method for quantitative detection of mutations in genomic regions of 300–600 bp", *Hum. Mol. Genet.*, 5(1):107–114.
Liu, Q., et al. (1997), "Inhibition of PCR Amplification by a Point Mutation Downstream of a Primer", *Bio Techniques*, 22(2):292–300.
Liu, Q., et al. (1997), "Overlapping PCR for Bidirectional PCR Amplification of Specific Alleles: A Rapid One–Tube Method for Simultaneously Differentiating Homozygotes and Heterozygotes", *Genome Research*, 7:389–398.

(List continued on next page.)

*Primary Examiner*—W. Gary Jones
*Assistant Examiner*—Janell E. Taylor
(74) *Attorney, Agent, or Firm*—Rothwell, Figg, Ernst & Manbeck

(57) ABSTRACT

Methods are presented for determining the presence of an inversion in the factor VIII gene which cause hemophilia A. The methods encompass long distance, multiplex PCR (including overlapping PCR). The use of deaza-dGTP, high levels of DNA polymerases and high levels of DMSO aid in successfully performing the PCR. The use of a novel technique called subcycling PCR can also be applied as part of the methods. The technique allows for the determination of whether a person is homozygous or hemizygous for the inversion and has hemophilia A or whether a person is heterozygous for the inversion and is a carrier. The technique of long distance, multiplex PCR including use of deaza-dGTP, high levels of DNA polymerases and high levels of DMSO are applicable to the determination of the presence of other gross chromosomal aberrations such as deletions/inversions, translocations and inversions. The use of subcycling PCR can achieve efficient and more even amplification than normal two or three temperature PCR and is applicable to long distance, multiplex PCR.

28 Claims, 12 Drawing Sheets

OTHER PUBLICATIONS

Liu, Q. and Sommer, S.S. (1994), "Parameters Affecting the Sensitivities of Dideoxy Fingerprinting and SSCP", *PCR Methods Appl.*, 4(2):97–108.

Naylor, J., et al. (1993), "Characteristic mRNA abnormality found in half the patients with severe haemophilia A is due to large DNA inversions", *Hum. Molec. Genet.*, 2(11):1773–1778.

Naylor, J.A., et al. (1995), "Investigation of the factor VIII intron 22 repeated region (int22h) and the associated inversion junctions", *Hum. Molec. Genet.*, 4(7):1217–1224.

Naylor, J.A., et al. (1996), "A Novel DNA Inversion Causing Severe Hemophilia A", *Blood*, 87(8):3255–3261.

Ochman, H., et al. (1988), "Genetic Applications of an Inverse Polymerase Chain Reaction", *Genetics*, 120:621–623.

Ochman, H., et al. (1990), "Inverse Polymerase Chain Reaction", *Bio/Technology*, 8:759–760.

Seemayer, T.A. (1990), "Polymerase Chain Reaction", *Pediatr. Pathol.*, 10(3):311–317.

Shuber, A.P., et al. (1995), "A Simplified Procedure for Developing Multiplex PCRs", *Genome Research*, 5:488–493.

Su, X., et al. (1996), "Reduced extension temperatures required for PCR amplification of extremely A+T–rich DNA", *Nucleic Acids Research*, 24(8):1574–1575.

Van de Water, N.S., et al. (1995), "Factor VIII Gene Inversions in Severe Hemophilia A Patients", *Pathology*, 27(1):83–85.

Yip, B., et al. (1996), "A semi–automated method for analysis of intron 13 and intron 22 dinucleotide repeat polymorphisms of the factor VIII gene", *Clin. Lab. Haematol.*, 18(2):111–114.

* cited by examiner

ALL THE EXPECTED TWENTY-SIX FRAGMENTS AND THEIR SIZES

|    | D1 1 |      | D2 116 |      | D3 216 |      | D4 313 |      | D5 465 |      | D6 591 |     |
|----|------|------|--------|------|--------|------|--------|------|--------|------|--------|-----|
| U1 | 840  | D1U1 | 852    | D2U1 | 737    | D3U1 | 637    | D4U1 | 539    | D5U1 | 387    | D6U1 | 262 |
| U2 | 709  | D1U2 | 721    | D2U2 | 606    | D3U2 | 506    | D4U2 | 408    | D5U2 | 256    | D6U2 | 131 |
| U3 | 591  | D1U3 | 603    | D2U3 | 488    | D3U3 | 388    | D4U3 | 280    | D5U3 | 138    |      |     |
| U4 | 438  | D1U4 | 450    | D2U4 | 335    | D3U4 | 235    | D4U4 | 137    |      |        |      |     |
| U5 | 313  | D1U5 | 325    | D2U5 | 210    | D3U5 | 110    |      |        |      |        |      |     |
| U6 | 209  | D1U6 | 224    | D2U6 | 109    |      |        |      |        |      |        |      |     |

SEQUENCE LISTING

<160> NUMBER OF SEQ ID NOS: 11

<210> SEQ ID NO 1
<211> LENGTH: 32
<212> TYPE: DNA
<213> ORGANISM: Homo sapiens

<400> SEQUENCE: 1
tgcccgtcag aagttctcca gcctctacat ct                                    32

<210> SEQ ID NO 2
<211> LENGTH: 32
<212> TYPE: DNA
<213> ORGANISM: Homo sapiens

<400> SEQUENCE: 2
ggtcaagact gaaattagcg tgttaggcaa ga                                    32

<210> SEQ ID NO 3

<211> LENGTH: 1319
<212> TYPE: DNA
<213> ORGANISM: Homo sapiens

<400> SEQUENCE: 3

| | | | | | |
|---|---|---|---|---|---|
| ccatacatta | gtaaaatcag | aatacatttg | aatttaccaa | gtaggaacaa | gagtattaag | 60 |
| tttactgccc | atgcatcagg | gcaatgttag | ctctcttgtt | ttctatcata | atatagactc | 120 |
| aagggacctc | aaacatcttt | acatcccaca | agcacaatgc | ctgtccatta | cactgatgac | 180 |
| attatgctga | caggatctgg | taaacacata | acaaataagc | ctgtcttgct | cttgactttta | 240 |
| atgagaatgt | aacctgtgtt | tcactgttta | atataatgtt | cactgttagt | ttcaaatact | 300 |
| ttttatgatg | tttaaaaagt | tttctcctat | ccctatttta | tttgcaatgg | caactgaatt | 360 |
| ttatcaaatg | cttttccagc | atctttgaca | tggtcacatt | tctcttttgt | gttgtcaaat | 420 |
| tatacttaac | attcaatagt | gtgctgacaa | gaaattaaca | acccacaggg | gagcaaagtg | 480 |
| agaagaggtt | aagaagtaaa | ggccttgatt | tatagcattg | gcagatttcc | ctgacataaa | 540 |
| tactactccc | atcatgcctg | gcccaggga | tgggaagaga | tgcttactta | caattggctc | 600 |
| tcacagacca | gtgcaagagc | actactgtgc | tccatttctg | ggaaaacttt | cgtcagtcat | 660 |
| agtgtgttag | ttatttaaaa | cttagctgga | tccaatttgc | caacatttca | tttataattt | 720 |
| ctatatctat | attcatgaat | gaaatggtt | tagcttttttc | agtagctcta | cttaccaggt | 780 |
| tttggcatga | gggttatatt | aaacttgaaa | ataaagtggg | aaagcttcca | ttttttttcca | 840 |
| tgaagactat | tgctctagaa | tagcttattt | aatgtaggaa | tccagtattt | aatgagagta | 900 |
| aatgaaaaag | ccatatgagc | catgtgcttt | atttagtgag | agatactagg | ctatattttc | 960 |
| caatcgttat | atgattattg | ctattctcat | ttgtgttgcc | ttgagttaat | gtctgcaaat | 1020 |
| gtgcacatta | gagtcatata | tcccttcctg | tgccatacat | ctatatctgt | atacacacat | 1080 |
| atgtcttttc | tcctttttttc | ccttctgtat | caagagttgg | caagtgtttg | tctattctat | 1140 |
| taattttttca | aagaatcagc | tcagtttttaa | acccaaacgt | ggttttgaaa | gagctgtttc | 1200 |
| tagttcatca | atctctgttc | aaaacttaa | aaattctatt | ttccttttctt | ttggtttgtt | 1260 |
| tcctacaatc | tggaggtgaa | tgcttagttc | acttattctt | caatctttgt | attttaacg | 1319 |

<210> SEQ ID NO 4
<211> LENGTH: 34
<212> TYPE: DNA
<213> ORGANISM: Homo sapiens
<220> FEATURE:
<221> NAME/KEY: misc_difference
<222> LOCATION: (1)..(2)
<223> OTHER INFORMATION: These two bases are added as part of a high GC
      tail and are not part of the genomic sequence.

<400> SEQUENCE: 4
cgaatcacct cccactaggc ccttccttca acag                              34

<210> SEQ ID NO 5
<211> LENGTH: 32
<212> TYPE: DNA
<213> ORGANISM: Homo sapiens

<400> SEQUENCE: 5
caccgttaga ggagaccagc agcccacaga ct                                32

<210> SEQ ID NO 6
<211> LENGTH: 695
<212> TYPE: DNA

<213> ORGANISM: Homo sapiens

<400> SEQUENCE: 6

```
taatcatcag ggaaatgcac attaaaacca caataagata ccaccttact cctgcaagaa      60
tggccattat taaaaagtca aaaagcaata gacgttggcg tggatgtggt gaaaagggac     120
ggtgcataca ctgctaggtg ggaatgtata acctctatgg gaaacagtat ggagattcct     180
taaagaacta aaagtagatc taccacgcga tccagcaatc ccactactgg gtatctgccc     240
aaaggagaag aagtcattat atgaaaaaca caatgcaca catatgttta tttcagcaca      300
attcacaaat gcaaagatat agaacgaacc gaagcaccaa tcaaccaatg agtagatata     360
gaaaatgtgg tatgtacaca ccgtggagaa ctactcagcc ataaagagaa acagaataat     420
gtcatttgca gcaacttgga tggagcttgg aggccattat tctaagtgaa gtaactcagg     480
aatggaagac caaattaccc tgtgttctca cctgtaagtg ggagctaagc tatgagaatg     540
caaagacata cagagtgata taatggactt tggagacaca caaggggaa gagtgtgagg      600
gtgtgggata agaaaactac atattgggta caatgtacac tactcgggtg atgggtgcac     660
taaaatctca gaatttacca ctatataatt catcc                                695
```

<210> SEQ ID NO 7
<211> LENGTH: 412
<212> TYPE: DNA
<213> ORGANISM: Homo sapiens

<400> SEQUENCE: 7

```
acaatgacaa cactatactg tgataagtgc tatgagaggg gaagttcaag gtgctggtta      60
tagtttggtt tgtttgaccc ctccaaatct catgtggaaa tttgataccc agtgttggaa     120
ggtggggtct aatggaaggt gtttgagtca tggggtggat ccttcatgaa tggcttggtg     180
ccagcctcgc agtaatgagt gagttctcac ttgattcatt cccacaagag ctggttgtta     240
aaaaagagtg tagcacctcc cccccacccc accttgattc ctctctcatc atgtgatctc     300
tgcacttgcc ggctcccctt caccttatgc catgagtgga agcagcctga daccctcacc    360
aagaaaccaa gcagatgcca gcaccatgtt tcctgtacag cctgcagaat ca             412
```

<210> SEQ ID NO 8
<211> LENGTH: 38
<212> TYPE: DNA
<213> ORGANISM: Homo sapiens
<220> FEATURE:
<221> NAME/KEY: misc_difference
<222> LOCATION: (1)..(4)
<223> OTHER INFORMATION: Bases 1-4 are part of a high GC tail and are
      not part of the genomic sequence.

<400> SEQUENCE: 8

```
gccctgcctg tccattacac tgatgacatt atgctgac                              38
```

<210> SEQ ID NO 9
<211> LENGTH: 39
<212> TYPE: DNA
<213> ORGANISM: Homo sapiens
<220> FEATURE:
<221> NAME/KEY: misc_feature
<222> LOCATION: (1)..(5)
<223> OTHER INFORMATION: Bases 1-5 are part of a high GC tail and are
      not part of the genomic sequence.

<400> SEQUENCE: 9

```
ggccctacaa ccattctgcc tttcactttc agtgcaata                             39
```

-continued

```
<210> SEQ ID NO 10
<211> LENGTH: 36
<212> TYPE: DNA
<213> ORGANISM: Homo sapiens

<400> SEQUENCE: 10
cacaaggggg aagagtgtga gggtgtggga taagaa                              36

<210> SEQ ID NO 11
<211> LENGTH: 40
<212> TYPE: DNA
<213> ORGANISM: Homo sapiens
<220> FEATURE:
<221> NAME/KEY: misc_difference
<222> LOCATION: (1)..(2)
<223> OTHER INFORMATION: Bases 1-2 are part of a high GC tail and are
      not part of the genomic sequence.

<400> SEQUENCE: 11
ccccaaacta taaccagcac cttgaacttc ccctctcata                          40
```

SINGLE TUBE PCR ASSAY FOR DETECTION OF CHROMOSOMAL MUTATIONS: APPLICATION TO THE INVERSION HOTSPOT IN THE FACTOR VIII GENE INCLUDING OPTIONAL USE OF SUBCYCLING PCR

CROSS REFERENCE TO RELATED APPLICATIONS

The present invention is a continuation-in-part of application Ser. No. 09/103,505 filed Jun. 24, 1998. This application claim benefit to provisional No. 60/113,669 filed Jun. 24, 1998.

BACKGROUND OF THE INVENTION

Hemophilia A is one of the most common coagulation disorders with an incidence of about one in 5,000 males. The disease is caused by mutations in the factor VIII gene located on the X chromosome. About half the families with severe disease have a large genomic inversion of the factor VIII gene which separates the first 22 exons from the final four exons. This inversion results from a hotspot of recombination between a 9.5 kb region in intron 22 (Int22h1) and either of two extragenic, distal homologs, Int22h2 and Int22h3 near the Xq telomere which are repeats of Int22h1. These repeated sequences are more than 99% identical with one another (Naylor et al., 1995). Int22h2 and Int22h3 are in the opposite orientation of Int22h1 and therefore recombination produces an inversion. Intrachromosomal homologous recombination occurs between Int22h1 and the distal extragenic homolog (Int22h3), or between Int22h1 and the proximal Int22h2 homolog (types 1 and 2 inversions, respectively) (Antonarakis et al., 1995; Naylor et al., 1993; Lakich et al., 1993). Some patients have more than two copies of the extragenic homologs causing inversion types 3A and 3B.

The inversions disrupt the factor VIII gene and cause almost half of all cases of severe hemophilia A. They are detected routinely by time-consuming and expensive Southern blots using a probe from Int22h1. A rapid and inexpensive test is of particular clinical utility because carrier testing is often paid out-of-pocket due to insurance issues and confidentiality. A low cost test may facilitate more optimal use of genetic services. Successful polymerase chain reaction (PCR) amplification spanning these regions has not been reported, presumably because the homologs contain a 3.5 kb GC island of 65% G+C content and there is a 1 kb region of 79% GC within the GC island (see FIG. 4).

A single-tube PCR assay is disclosed that combines multiplex PCR with long distance PCR (Cheng et al., 1994; Barnes, 1994) to differentiate wild-type males and females from affected males and from carrier females (FIG. 3A).

Multiplex PCR is a rapid and convenient method, but uneven amplification is common (Chamberlain et al., 1998). Efforts have been made to achieve uniform amplification. Since primer concentration is often difficult to optimize, Shuber et al. (1995) developed a simplified optimization procedure based on the use of chimeric primers. Each primer contains a 3' region complementary to sequence-specific recognition sites and a 5' region made up of a universal 20-nucleotide sequence. Each individual PCR was first optimized by adjusting primer concentrations, cycling times, and annealing temperatures (Shuber et al., 1995). In another approach, two detergents, DMSO and betaine, were combined to achieve uniform amplification for three templates differing in GC contents (Baskaran et al., 1996). Additional approaches include adjusting the annealing temperature, KCl (salt) concentration, and primer concentration for each locus encountered in developing multiplex PCR of small sizes (Henegariu et al., 1997). The instant disclosure sets out a detailed, novel method, termed S-PCR, to more evenly and efficiently amplify the multiplex segments. Although S-PCR results in more even amplification, it is not a necessary step in any of the assays described herein.

The publications and other materials used herein to illuminate the background of the invention or provide additional details respecting the practice, are incorporated by reference, and for convenience are respectively grouped in the appended List of References.

SUMMARY OF THE INVENTION

The present invention provides methods for performing long distance, multiplex PCR to detect the presence of chromosomal abnormalities such as inversions, deletions/inversions and translocations.

In one aspect of the invention, chromosomal deletions/inversions are detected by performing long distance, multiplex PCR using primers which flank the site of the deletion/inversion, wherein the PCR products are used to detect the presence of the deletion/inversion.

In accordance with another aspect of the invention, inversions within a chromosome are detected by performing long distance, multiplex PCR using primers which flank the site of the inversion, wherein the pattern of PCR products which result are used to detect the presence or absence of said inversion.

In accordance with yet another aspect of the invention, translocations between two chromosomes are detected by performing long distance, multiplex polymerase chain reaction using primers which flank the site of the chromosomal breakpoints of the translocation, wherein the pattern of PCR products enables one to determine whether a translocation is present.

Other aspects of the invention are specifically directed to determining the presence of an inversion in the factor VIII gene which causes hemophilia A. These methods comprise performing long distance PCR with 2 primers, 3 primers, 4 primers, or more than 4 primers. These methods allow one to detect the presence of males who have the inversion and therefore have hemophilia A and these methods allow one to determine whether females are carriers of the inversion.

A further aspect of the invention is the use of relatively high levels of DMSO, relatively high levels of DNA polymerases, and/or the use of deaza-dGTP in long distance PCR.

The invention also provides a method of PCR, called subcycling PCR, wherein the temperature of the elongation step (or of a combined annealing/elongation step) is subcycled between at least two temperatures wherein these temperatures are below the denaturation temperature of the PCR product for each full cycle of PCR.

Yet a further aspect of the invention is the determination of DNA sequences flanking intron 22 of the factor VIII gene (Int22h1) and of sequence flanking homologs (Int22h2 and Int22h3) of this region.

Another aspect of the invention is that the long distance, multiplex PCR can be performed in a single reaction vessel.

Yet another aspect of the invention is the determination of primers which are useful in performing long distance PCR to determine the presence of an inversion in the factor VIII gene which inversion causes hemophilia A in males.

A PCR assay method is presented for detecting the inversion in the factor VIII gene which is a common cause of hemophilia A. This protocol comprises a novel single-tube PCR assay that combines overlapping PCR with long distance PCR to differentiate the wild-type, inversion and carrier. The PCR amplifies overlapping and multiplex segments of PQ (12 kb), AB (10 kb), PB (11 kb) and AQ (11 kb) with four primers P, Q, A and B directly from genomic DNA template. Performing a PCR assay to detect this inversion is challenging due to the size of the amplification (10–12 kb), the varying GC content (30–80%) and the multiplex PCR products involved (four for carrier female) and performance of a successful PCR across this region has not been previously reported. Efficient amplification of the four segments depends on three modifications to standard long distance PCR protocols: i) relatively high concentrations of DMSO; ii) addition of deaza-dGTP; and iii) relatively high concentrations of Taq/Pwo DNA polymerases. One of the segments was amplified much more efficiently than the others under standard three-temperature cycling conditions (12 seconds at 94° C., 30 seconds at 65° C., 14 minutes at 68° C.). To facilitate the uniform amplification of the multiple regions, subcycling-PCR (S-PCR) was developed. In S-PCR, the combined annealing/elongation step (or the elongation step alone if annealing and elongation are performed at separate temperatures) is composed of subcycles of shuttling between a low and a high temperature wherein these subcycling temperatures remain below the denaturation temperature, e.g., shuttling four times between 60° C. and 65° C. S-PCR produces consistent robust amplification of the various segments produced by wild-type, mutant, and carrier individuals. S-PCR generally may be advantageous in three contexts: i) amplification of long segments in which the GC content varies within the segment; ii) multiplex amplification of long segments; and iii) multiplex amplification of short segments in which the GC content varies among the segments. These methods are generally applicable to any PCR reactions in which the foregoing considerations apply.

BRIEF DESCRIPTION OF THE FIGURES

FIG. 8A shows the results of a standard three-temperature PCR. The 1×concentration of the four primers were 0.4, 0.4, 0.12 and 0.12 μM, respectively, for P, Q, A and B. FIG. 8B shows the results of using S-PCR. The 1×concentration was 0.2 μM for each primer. M is a size marker of 9.4 kb.

SUMMARY OF SEQUENCE LISTING

Figure 1A:
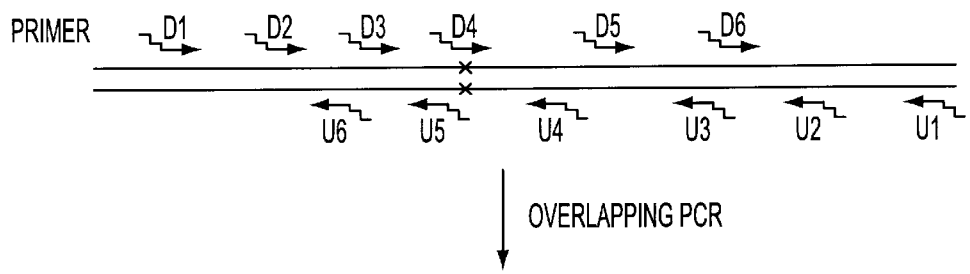
FIG. 1A illustrates the original format of performing overlapping PCR. Multiple primers are used with a single template.

SEQ ID NO:1 is a primer corresponding to a portion of exon 22 of the factor VIII gene and was used in combination with SEQ ID NO:2 to obtain 5' flanking sequence of the 9.5 kb homologous repeat of intron 22.

SEQ ID NO:2 is a primer corresponding to a portion of intron 22 of the factor VIII gene as was used in combination with SEQ ID NO:1 to obtain 5' flanking sequence of the 9.5 kb homologous repeat of intron 22.

SEQ ID NO:3 shows 1319 bp of 5' flanking sequence of the 9.5 kb homologous repeat of intron 22. The first base of GenBank Accession No. X86011 is immediately after the last base of this sequence. This sequence runs from base –1369 to base –51 before the homologous repeat.

SEQ ID NO:4 is a primer corresponding to a portion of intron 22 and was used in conjunction with SEQ ID NO:2 and SEQ ID NO:5 to amplify a DNA fragment containing Int22h2 in order to determine the flanking sequence of Int22h2.

SEQ ID NO:5 is a primer corresponding to a portion of intron 22 and was used in conjunction with SEQ ID NO:4 to determine the flanking sequence of Int22h2.

SEQ ID NO:6 shows 695 bp of 5' flanking sequence of Int22h2. This sequence runs from base –745 to base –51 before the homologous repeat.

SEQ ID NO:7 shows 412 bp of 3' flanking sequence of Int22h2. This sequence runs from base +51 to base +462 following the homologous repeat.

SEQ ID NO: 8 is primer P used in PCR reactions. This also corresponds to bases 158–191 of SEQ ID NO:3 and is approximately 1.2 kb 5' to the 9.5 kb Int22h1. The first 4 bases (gccc) are part of a high GC tail and are not of the 5' flanking sequence of Int22h1.

SEQ ID NO:9 is primer Q used in PCR reactions. This corresponds to bases 8799–8832 of GenBank Accession No. X86012 and is approximately 1.3 kb 3' to the 9.5 kb Int22h1. The first 5 bases (ggccc) are part of a high GC tail and are not part of the 3' flanking sequence of Int22h1.

SEQ ID NO:10 is primer A used in PCR reactions. This corresponds to bases 579–614 of SEQ ID NO:6 and is approximately 0.2 kb 5' to the 9.5 kb Int22h2 and Int22h3.

SEQ ID NO:11 is primer B used in PCR reactions. This corresponds to bases 31–68 of SEQ ID NO:7 and is approximately 0.1 kb 3' to the 9.5 kb Int22h2 and Int22h3. The first 2 bases (cc) are part of a high GC tail and are not part of the 3' flanking sequence of Int22h2 or Int22h3.

DETAILED DESCRIPTION OF THE INVENTION

Figure 3A:
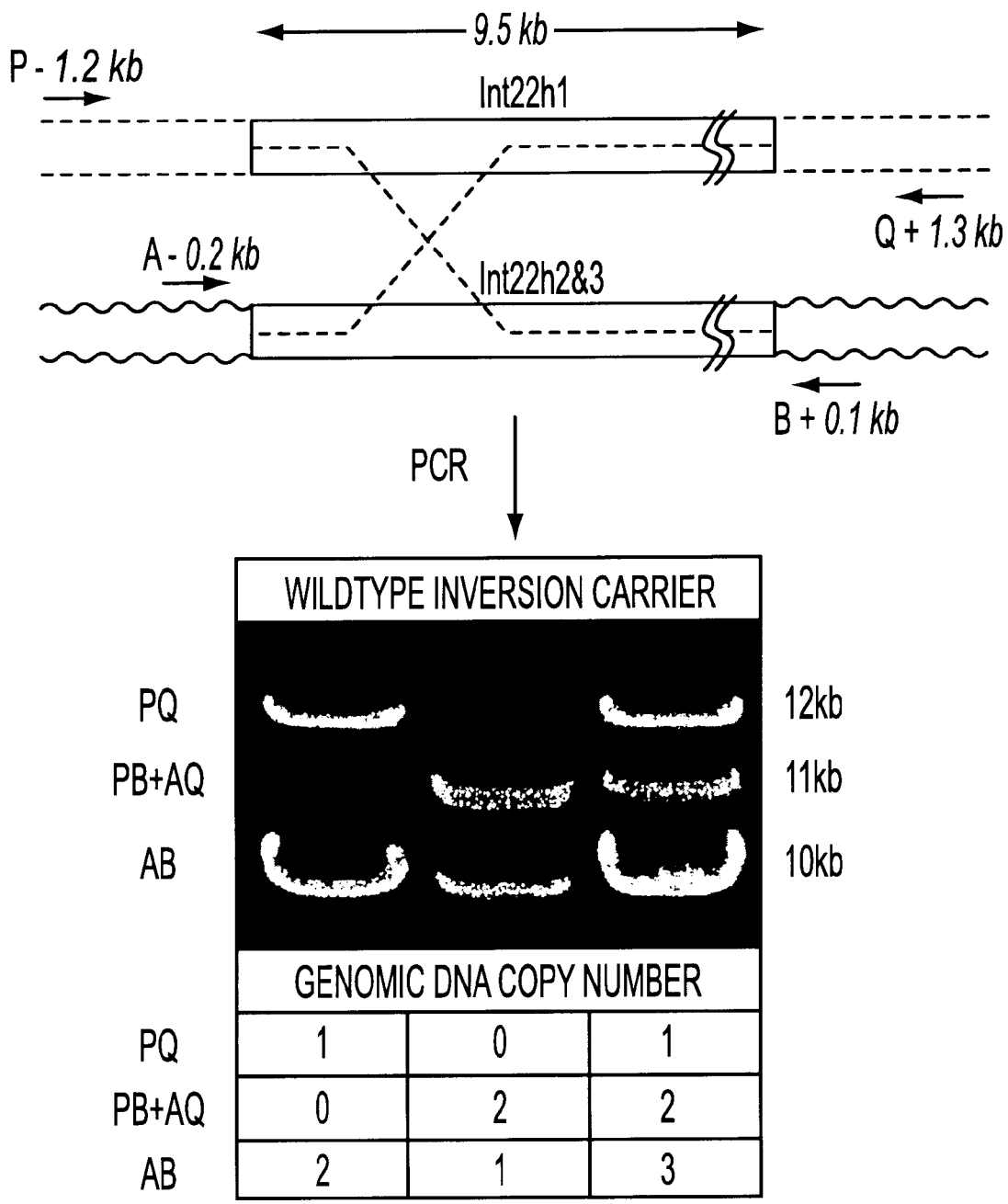
FIG. 3A is a schematic of the PCR assay. At the top, the locations of four primers (P, Q, A and B) are represented by arrows and their positions are indicated. The upper box represents Int22h1 and the dashed lines indicate the flanking sequences. The lower box represents Int22h2 and Int22h3 and the wavy lines indicate the flanking sequences. Deleterious inversions can occur by recombination between Int22h1 and either Int22h2 or Int22h3 (dotted lines). The PCR amplifies overlapping and multiplex segments from genomic DNA with four primers P, Q, A and B to generate four potential segments PQ, AB, PB and AQ. Two primers, P and Q, are specific to the flanking sequences of Int22h1, and located at −1212 bp before and +1334 bp after the homolog; and two primers, A and B, are specific to the flanking sequences of Int22h2 and Int22h3, located at −167 bp before and 118 bp after the homologs. P and Q anneal at different distances from A and B in order to differentiate PQ (12 kb), AB (10 kb) and PB and AQ (11 kb each) segments on agarose gels. Genomic DNA from wildtype, male patient (inversion) or female carrier samples produces three patterns of amplification. PQ is produced in a wildtype sample and PB+AQ is generated in males with the inversion. But both PQ and PB+AQ are present in the carriers. AB is always produced and serves as a positive control, because at least one copy of either Int22h2 or Int22h3 remains intact. S-PCR was performed with each primer at 0.2 $\mu$M. The relative copy numbers of segments PQ, AB and PB+AQ before amplification are indicated below, although some individuals have one or more extra copies of Int22h2 or Int22h3 located on the X chromosome or autosome. Similar results were obtained using three-temperature PCR with its optimal primer concentrations (0.4, 0.4, 0.12 and 0.12 $\mu$M of P, Q, A and B, respectively) and using two-temperature PCR with its optimal primer concentrations (0.2, 0.2, 0.15 and 0.15 $\mu$M of P, Q, A and B, respectively).

We have developed a single-tube PCR assay that combines overlapping PCR (Liu et al., 1997b) with long distance PCR (Barnes, 1994) to achieve the genetic diagnosis of chromosomal inversions, such as, for example, those associated with hemophilia A (FIG. 3A). The method allows the use of multiplex PCR in a single-tube rather than requiring the use of several different tubes in which only a single pair of primers is used in each tube. This method is simple, rapid, reproducible, inexpensive, non-isotopic and amenable to automation. This test is of significant clinical utility for the approximately 100,000 females in the United States who are at risk for hemophilia A. The test is 5 to 10 fold faster than the current assay which is performed by Southern blotting. This approach can be used to detect other types of chromosomal rearrangements such as deletions/inversions and translocations.

The inversion was detected by performing PCR directly from genomic DNA with four primers which differentiate the wildtype, inversion and carrier. Two primers, P and Q, are located within the factor VIII gene at positions –1212 bp and +1334 bp flanking Int22h1. Two primers, A and B, are located at –167 bp and +118 bp flanking Int22h2 and int22h3. Segments PQ (12 kb) and AB (10 kb) are produced in hemizygous wildtype males. Males with hemophilia A due to the inversion produce PB (11 kb) and AQ segments (11 kb) along with the 10 kb AB segment from the nonrecombined extragenic homolog. Female carriers produce PQ, PB+AQ and AB segments. In all cases, an AB segment serves as an internal control because at least one copy of Int22h2 or Int22h3 remains intact. The three segment sizes are readily separated on a 0.6% agarose gel. High yield and reproducible amplification depended on three unusual modifications to standard long distance PCR protocols: i) relatively high concentrations of DMSO additive; ii) substantially increased amounts of Taq and Pwo DNA polymerases; and iii) deaza-dGTP.

Methods of performing PCR are detailed wherein the methods include modifications, including a novel step of subcycling the temperature within each full cycle of PCR, which enable improved results i) when performing PCR across a long region encompassing varying GC content, ii) when performing multiplex amplification of long segments so as to yield more uniform amplification of the different fragments, and iii) multiplex amplification of short segments in which the GC content varies among the segments so as to yield more uniform amplification of the different fragments. To demonstrate these improved methods, examples are set out which detail the methods as applied to performing multiplex PCR to detect an inversion in the factor VIII gene which causes hemophilia A.

Figure 1B:
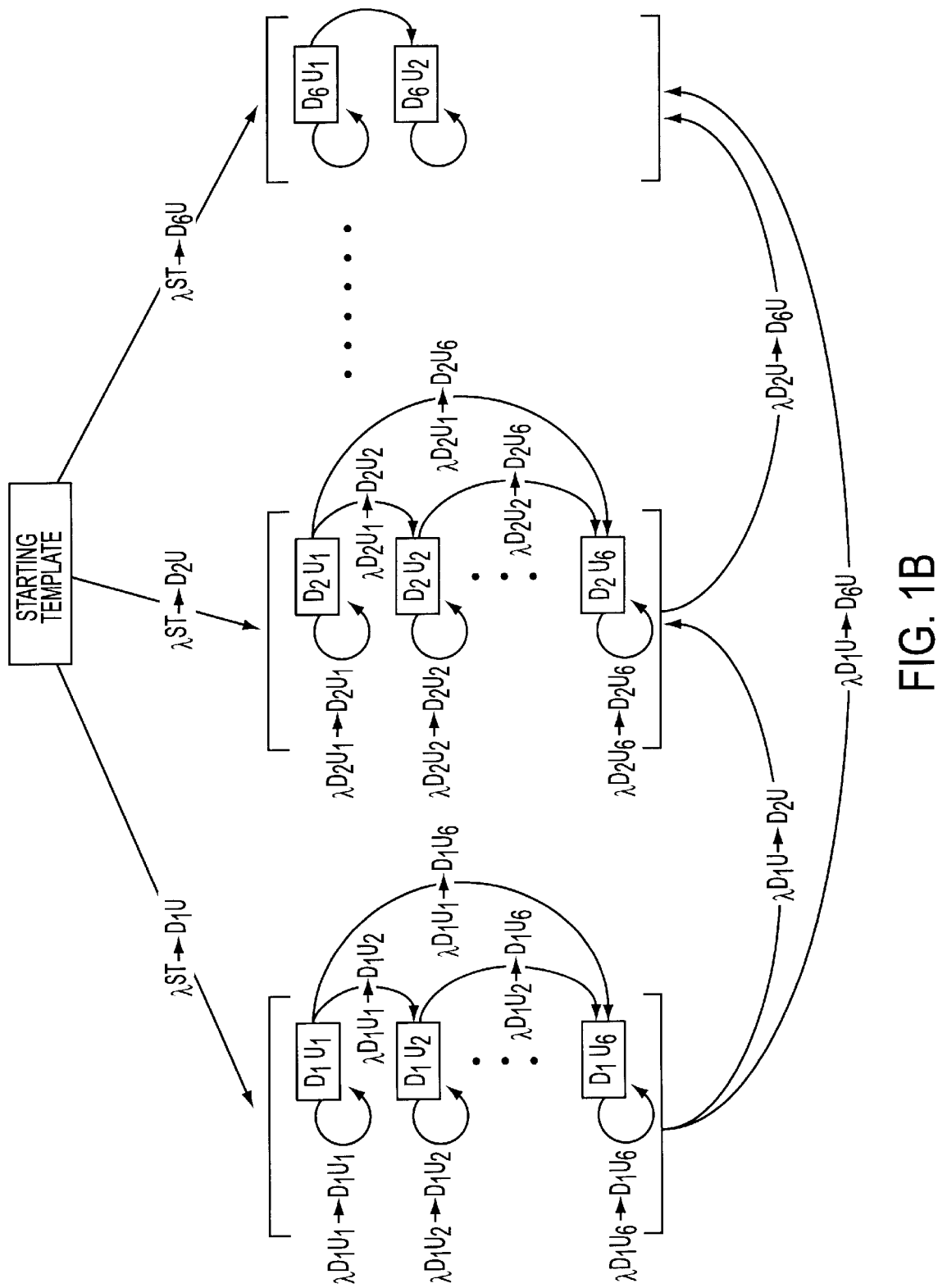
FIG. 1B illustrates the self-amplification and transfer-amplification of the PCR products which form as a result of using the original method of overlapping PCR as shown in FIG. 1A.

One aspect of the invention is the combination of a form of overlapping PCR with long distance PCR. Three forms of overlapping PCR are set out in Table 1. The original form of overlapping PCR is outlined in FIG. 1A. In this format several primers are used which all bind to the nucleic acid region of interest with some primers corresponding to the sense strand and others to the antisense strand. Many overlapping products result from performing the PCR. In the Example shown in FIG. 1A, a total of 26 distinct products are possible. Only a single template is used in this format of overlapping PCR. During the early cycles, the larger products which form become templates not only for producing the larger products but also for the smaller products thereby resulting in what is termed "transfer amplification". This concept is shown in FIG. 1B. The method incorporates 5' mismatch of the primers to prevent megapriming. All of the primers have tails added. This form of overlapping PCR works best for nucleic acids up to about 1 kb in length.

Figure 2A:
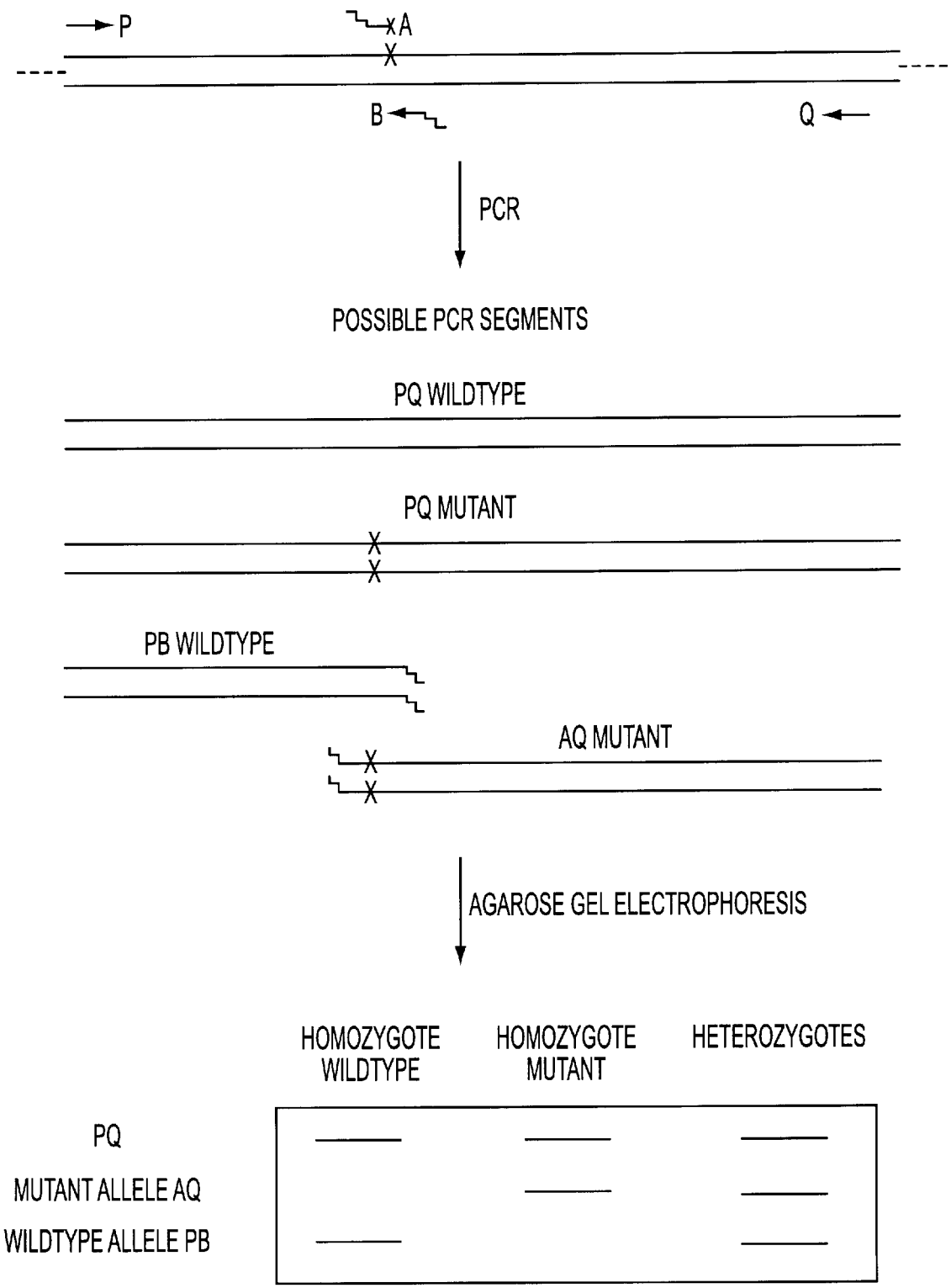
FIG. 2A illustrates Bi-PASA PCR. Two templates are shown (a wild-type and a mutant form, here a missense mutation, of the same gene). Primers P and Q hybridize to both templates whereas primer A is specific for the mutant template and primer B is specific for the wild-type template. The three possible PCR products which can be produced are illustrated.
Figure 4:
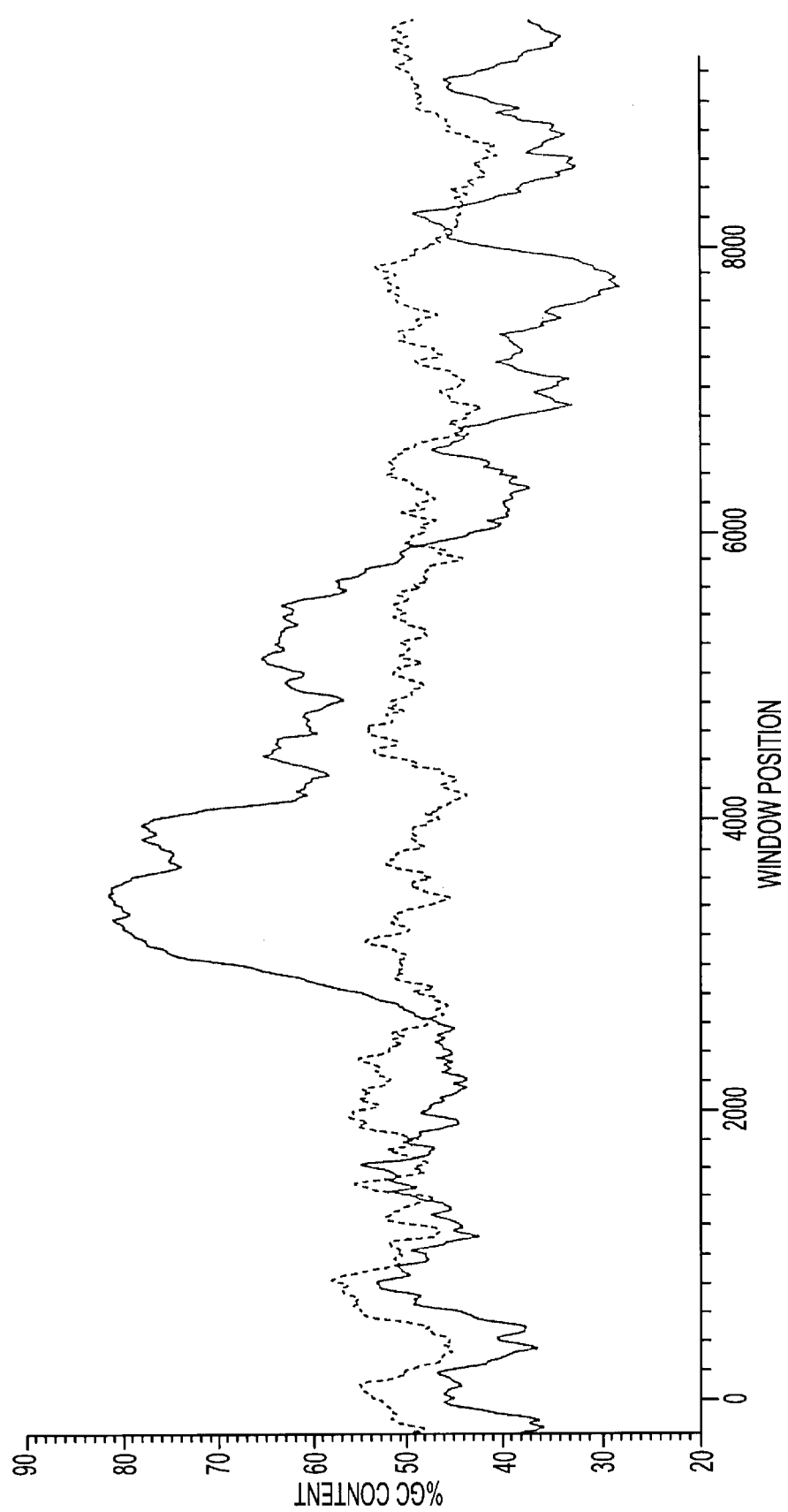
FIG. 4 is a mapplot of the GC content of segment AB. The Y-axis indicates the GC content of the sequential windows of 300 nucleosides for the range −167 to 9621 using a sliding analysis window of 300 symbols and smoothed by a 21 symbol moving average filter. The solid line plots the GC content of segment AB and the dotted line plots the GC content of segment AB after random shuffling.

A second type of overlapping PCR is referred to as "Bi-PASA PCR" which stands for bidirectional PCR amplification of specific alleles (Liu et al., 1997a). This method is outlined in FIG. 2A. This method utilizes up to 2 templates, e.g., a wild-type version and a mutated version of a gene. In the method shown in FIG. 2A, 4 primers are used for detecting a point mutation. The outer primers P and Q each hybridize to both versions of the template, i.e., to both the wild-type and the mutant templates. The inner primers A and B are template specific with A hybridizing only to the mutant version and B hybridizing only to the wild-type version. The number of different products formed is dependent upon the sample being assayed. If the sample wild-type Int22h1), AB (from wild-type Int22h2 or Int22h3), and PB and AQ which result from the inverted forms of Int22h1 and Int22h2 (or Int22h3). Transfer amplification does not occur in this type of overlapping PCR with each template being able to reproduce itself only and none of the other products. The method does use 5' mismatch of PCR product to prevent megapriming and this may be accomplished via addition of a tail to the 5' end sequence. Therefore primers may or may not be tailed. This method combines overlapping PCR with long distance PCR and is especially useful for templates greater than 4 kb although it can also be used with shorter templates.

It should be noted that Bi-PASA PCR requires some allele specific primers which limits the method to assaying for a specific point mutation at a known position. With the method disclosed herein, referred to as long distance, overlapping PCR, there is no need for such exact knowledge. The mutation can occur anywhere in the region between the primers and the primers can be widely spaced. In the examples concerning the intron 22 inversion in the factor VIII gene, the primers are on the order of 10–12 kb apart which leaves a lot of leeway, the complete intron of 9.5 kb in this case, within which the recombination event can occur. One need not know the exact location of the recombination site. The identical results will result regardless of where within the intron the recombination occurs. This is a distinct advantage of long distance, overlapping PCR as compared to the earlier 2 versions of overlapping PCR.

TABLE 1

Comparison of Overlapping PCR with Its Extensions

Figure 2B:
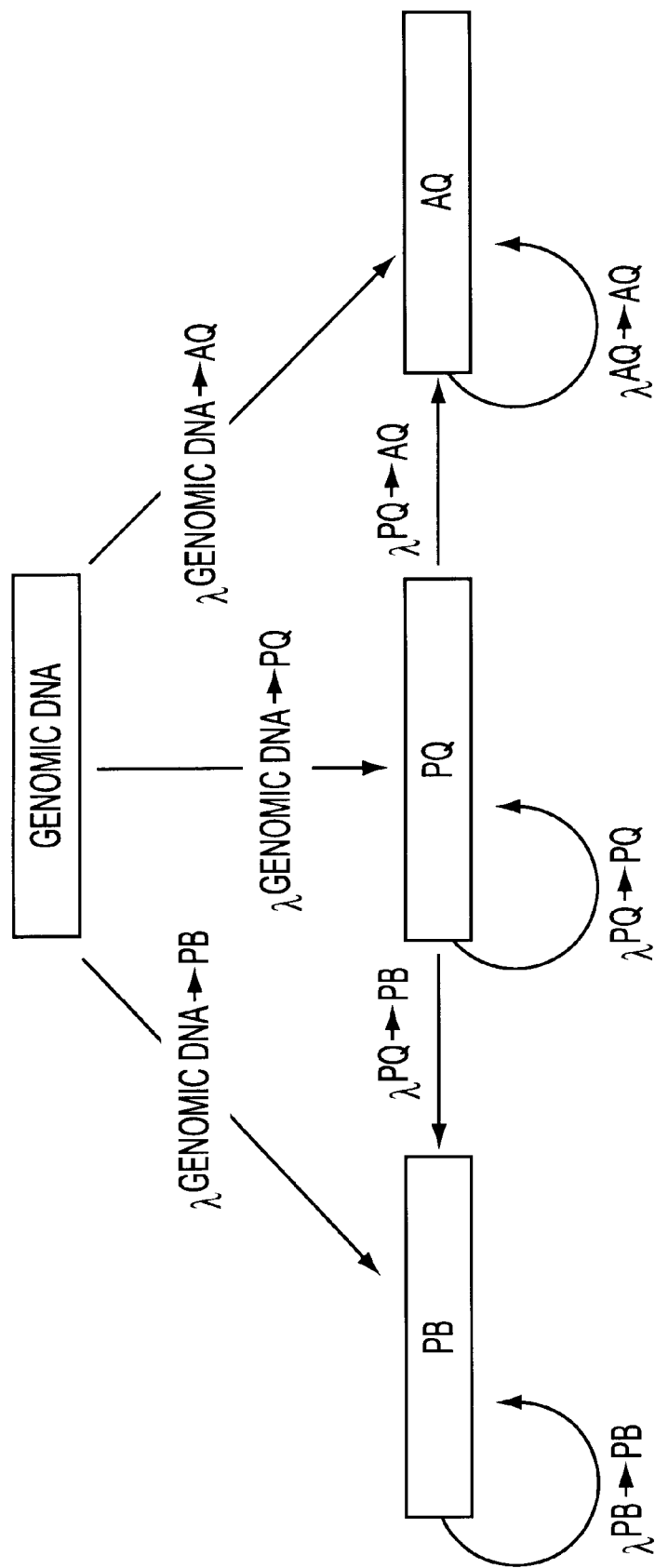
FIG. 2B illustrates the self-amplification and transfer-amplification of the PCR products which form. In this example transfer amplification can occur only from PQ (both with and without the mutation) to yield AQ and PB.

| | | | Characteristics | | | | |
|---|---|---|---|---|---|---|---|
| Type | Overlapping Products | Type of starting template | Transfer-amplification | 5' mismatch to prevent megapriming | Tailed primer | Hybrid with Original | Size |
| Original | Yes, up to tens | 1 | Yes, in early cycles | By tail | All the primers | — | 1 kb |
| Bi-PASA | Yes, up to 4 | Up to 2 | Yes, in early cycles | By tail | Two out of four primers | PASA | 1 kb |
| Long-distance, overlapping | Yes, up to 4 | Up to 4 | No | By 5' end sequence or by tail | No and Yes | Long distance PCR | >4 kb | is wild-type homozygous, the products will be PQ and AB. If the sample is mutant homozygous the products will be PQ and AQ. If the sample is heterozygous then PQ, AQ and PB will all be produced. As with the original method of overlapping PCR, Bi-PASA PCR also results in transfer amplification with the long PQ products acting as templates not only for more PQ but also for AQ and PB (see FIG. 2B). The method uses 5' mismatch to prevent megapriming and 2 of the 4 primers have tails. The method is a combination of the original form of overlapping PCR and PCR amplification of specific alleles. This method is most effectively used on templates of up to about 1 kb.

The third format of overlapping PCR is a novel method which is disclosed herein and is used in the assay for hemophilia A as discussed in the Examples below. This method is referred to as long distance, overlapping PCR. This method is shown in FIG. 3A. Here there can be up to 4 templates involved with 4 overlapping products resulting. FIG. 3A shows the example of the inversion in intron 22 of the factor VIII gene which results in hemophilia A in men with the inversion. The templates are wildtype Int22h1 and wildtype Int22h2 (or Int22h3) plus these templates with the inversions as a result of homologous recombination. The 4 overlapping products which can be produced are PQ (from To perform the assays necessary to detect an inversion in the factor VIII gene, the sequence flanking the regions Int22h1, Int22h2 and Int22h3 was obtained so that primers could be designed to amplify across these regions. The PCR conditions were modified so that the PCR would be successful. The modifications, which are set out in greater detail in the following Examples, include the modification of the cycling conditions during the PCR with the introduction of the novel step of subcycling the annealing and elongation steps at two or more temperatures during each full cycle of PCR, use of DMSO and deaza-dGTP in the reaction mixes, and adjustment of the amounts and types of DNA polymerases. By modifying and optimizing each of these parameters, including use of the novel subcycling steps, it was possible not only to amplify successfully across the factor VIII region which is involved in inversions resulting in hemophilia A, but it was possible to reduce or eliminate differential amplification of the several products which are produced such as in a female carrier which can yield four distinct PCR products when two pairs of primers are used concurrently.

The PCR method works at least as well as a Southern blot analysis. A blinded analysis of 40 DNA samples was performed. The PCR results were in complete concordance with Southern blot analysis for detection of wildtype, homozygotes and heterozygotes of the factor VIII gene inversion. Thirteen samples were hemizygous for the inversion, six carried the inversion, and 21 were wildtype, as determined by standard southern blot analysis. The PCR analysis was performed in less than one day with complete concordance with the Southern blot results. The amount of template DNA is another factor affecting the relative yields of the products (see also Chamberlain et al., 1998). The PQ, AB and PB+AQ segments were amplified from the carrier DNA template using as little as 25 ng genomic DNA per 25 µL reaction, which is 400-fold less than that required for the Southern blot analysis.

Definitions

Long distance, multiplex PCR refers to performing a polymerase chain reaction in which 3 or more primers are used and wherein at least one PCR product is at least 4 kb in length. Multiplex PCR also includes within its meaning overlapping PCR (Liu et al., 1997a) which is a subset of multiplex PCR.

The phrase "overlapping PCR" is meant to indicate a polymerase chain reaction in which some of the products which are formed partially include the same sequence as each other, i.e., at least two of the products have overlapping sequence. This can occur in different ways. For example, use of 3 primers wherein 2 primers are near a 5'-end of a sequence but at different locations and the third primer is oriented in the opposite direction near the 3'-end of the sequence. Performing PCR will result in production of 2 fragments which overlap each other. Use of more than 3 primers can result in many different fragments being produced, many of which will overlap other of the produced fragments. A second manner in which overlapping products may be formed is if PCR is performed on a diploid genome which is heterozygous for an inversion, duplication or translocation. For example, in assaying for a translocation between chromosome 7 and 17, if 4 primers are utilized (one primer for each side of the breakpoint in each of the two chromosomes), then 4 PCR products should be produced from a heterozygote—1) a product from the normal chromosome 7, 2) a product from the normal chromosome 17, 3) a product from one of the resulting recombinant chromosomes including 5'-end of chromosome 7 and 3'-end of chromosome 17, and 4) a product from the other recombinant chromosome including 5'-end of chromosome 17 and 3'-end of chromosome 7. Products 3 and 4 each overlap each of products 1 and 2. An example of overlapping PCR is shown in FIG. 3A for the case of an inversion resulting from homologous recombination between intron 22 of the factor VIII gene and one of its 2 homologs. Because this intron has 2 separate homologs, one homolog remains wild-type while the other is involved in recombination with the gene. The result is that using the 4 primers illustrated yields overlapping PCR products (i.e., some of the products are identical across part of their sequences) when an assay is performed on a sample which contains an inversion in this region. This last situation is explained in further detail in the Examples. It is to be noted that overlapping PCR is a subset of multiplex PCR.

The terms "upstream" and "downstream" are terms which are relative to each other and simply mean regions which are on either side of specified site. For example, upstream of an intron means chromosomal region flanking one end of an intron and downstream of an intron means chromosomal region flanking the other end of the intron.

Subcycling PCR refers to a polymerase chain reaction which has been modified to include a step of cycling of temperature within the elongation step or within the combined annealing/elongation step, this being referred to as a subcycling step. This subcycling of temperature is performed at temperatures below the denaturation temperature of the PCR product.

The expression "corresponds to" as applied to nucleic acids means that the nucleic acid has the same sequence as another nucleic acid which it "corresponds to" or it has the same sequence as the antisense strand of another nucleic acid which it "corresponds to". If a primer corresponds to a chromosome, it means that the primer comprises the same sequence as a portion of one strand of the chromosome.

The term "homologous" refers to a nucleic acid which has a sequence which is similar to a second nucleic acid. The two nucleic acids are "homologs" of each other. Homologs are at least 50% identical, preferably 80% identical, more preferably 95% identical and most preferably 99% identical with each other.

The phrase "specific for" means that a nucleic acid which is specific for a site will bind to that site only or to other sites which have an identical sequence to that site. Primers which are specific for amplifying a region of a chromosome will amplify only that single region of the chromosome or may also amplify homologous regions if the primers fall within the homologous regions.

The phrase "relatively high" as applied to DMSO concentration means a concentration of at least 6% DMSO, preferably in the range 6–9% DMSO.

The phrase "relatively high" as applied to DNA polymerase concentration means a concentration of at least 0.05 units per microliter of final reaction mixture, preferably in the range 0.05–0.4 units per microliter, and more preferably in the range 0.2–0.4 units per microliter.

EXAMPLE 1

Sequence for Flanking Regions of Factor VIII Gene Int22h1. Int22h2 and Int22h3

Fifty bp of 5' flanking sequence of Int22h1 in intron 22 was available from GenBank (Accession Nos. X86011 and X86012). Fifty bp of flanking sequences were also known at both 5' and 3' ends of Int22h2 and Int22h3 (Naylor et al., 1995). Inverse-PCR (Ochman et al., 1988) was applied to amplify the unknown flanking sequences.

To obtain sequence for 5' flanking Int22h1, a 6 kb segment was amplified with the Expand™ Long Template PCR system (Boehringer Mannheim). The primers used were:

F8(E22)(89)32D: 5'-TGCCCGTCAGAAGTTCTCCA-GCCTCTACATCT-3' (SEQ ID NO:1) (bases 89–120 of Genbank Accession No. M88644) which is a primer corresponding to exon 22 of the factor VIII gene and Int22h(365)32U: 5'-GGTCAAGACTGAAATTAGCG-TGTTAGGCAAGA-3' (SEQ ID NO:2) (bases 384–415 of GenBank Accession No. X86011) which corresponds to the 5' region of Int22h1. An ABI Model 377 sequencer was utilized to obtain 1319 bp of the 5' flanking sequence with four sequencing primers. This sequence of 1319 bp is shown as SEQ ID NO:3 in the Sequence Listing.

To obtain sequences flanking Int22h2 and Int22h3, inverse-PCR was utilized (Ochman et al., 1988). Wild-type female genomic DNA was digested by BclI restriction endonuclease. The products were electrophoresed through a 0.7% agarose gel, pieces of the gel were cut based on sizes of DNA markers, and then 14 kb DNA fragments containing Int22h2 were isolated by QIAEX II (QIAGEN). After circularization by T4 ligase, a 6 kb segment was amplified by two outward primers and then by half-nested primers. The two outward primers are:

Int22h(8250)34D: 5'-cgAATCACCTCCCACTAGGCCC-TTCCTTCAACAG-3' (SEQ ID NO:4) (bases 6245–6276 of GenBank Accession No. X86012) and Int22h(365)32U: 5'-GGTCAAGACTGAAATTAGCGTG-TTAGGCAAGA-3' (SEQ ID NO:2) (bases 384–415 of GenBank Accession No. X86011).

The half-nested primers are:

Int22h(8250)34D: 5'-cgAATCACCTCCCACTAGGCCC-TTCCTTCAACAG-3' (SEQ ID NO:4) (bases 6245–6276 of GenBank Accession No. X86012) and Int22h(267)32U: 5'-CACCGTTAGAGGAGACCAGCA-GCCCACAGACT-3' (SEQ ID NO:5) (bases 317–286 of GenBank Accession No. X86011).

Direct sequencing of the amplified product with two sequencing primers yielded 695 bp of the 5' flanking sequence and 412 bp of the 3' flanking sequence of Int22h2. These are shown as SEQ ID NO:6 and SEQ ID NO:7, respectively, in the Sequence Listing. These sequences were confirmed to be identical to those of Int22h3 by PCR amplifications.

EXAMPLE 2

Primer Design for the PCR Assay

Four primers are used in a multiplex PCR assay to detect the inversion in the factor VIII gene. These primers are labeled P, Q, A and B and their locations are indicated in FIG. 3A. These primers were designed with the aid of Oligo 5 software (National Biosciences). The $T_m$ value of each PCR segment was estimated by the formula of Wetmur: $T_m^{product}=81.5+16.6 \log [K^+]+0.41\% (G+C)-675/length$ (Wetmur, 1991). The G+C content of the AB segment is 51% on average and the $T_m$ is 81° C. The $T_m$ values of the primers were estimated by the nearest neighbor method at 50 mM KCl and 250 pM DNA with the formula: $T_m^{primer}=\Delta H/\{\Delta S+ R\times \ln(C/4)\}+16.6 \log [K^+]-273.15$ (Breslauer et al., 1986; Freier et al., 1986). Each primer was designed to have a $T_m$ that was 10° C. lower than the average $T_m$ of the PCR products (73° C.). Primer lengths varied from 36–40 nucleotides. For primers P, Q and B, a high GC tail of two to five nucleotides was added in order to achieve $T_m$ value of 73° C. Formation of primer dimers was minimized by designing each primer to have no more than four nucleotides complementarity to the 3' end of any of the other three primers. In addition, the 3' end of each primer had no more than four bases of intraoligonucleotide complementarity. Finally, there were no more than six bases of complementarity at the 3' end of any primer for any of the PCR products. The positions and sequences of the oligonucleotides are as follows:

P(−1212): 5'-gcccTGCCTGTCCATTACACTGATGA-CATTATGCTGAC-3' (SEQ ID NO:8),

Q(+1334): 5'-ggcccTACAACCATTCTGCCTTTCAC-TTTCAGTGCAATA-3' (SEQ ID NO:9),

A(−167): 5'-CACAAGGGGGAAGAGTGTGAGGG-TGTGGGATAAGAA-3' (SEQ ID NO:10), and B(+118): 5'-ccCCAAACTATAACCAGCACCTTGAACTTCCC-CTCTCATA-3' (SEQ ID NO:11). The high GC tails are indicated as lower case letters. The primer's first base at the 5' end of the sequence-specific region is assigned, wherein a "−" represents a distance before the homolog and a "+" represents a distance after the homolog.

Those of skill in the art recognize that similar primers can also be used successfully. For example, using the software called Oligo 5.0 (Oligo 5.0 primer analysis software program (NBI)), an analysis was performed to see if primer B could be just bases 1–36 of SEQ ID NO:11. The analysis did not show any obvious changes between the 40 base primer SEQ ID NO:11 and the shorter 36 base primer. The aspects analyzed included primer dimer and hairpin formation among the four primers (P, Q, A and B), the $T_m$ value, internal stability and false priming sites of the 36 base primer. This same analysis can be performed on other prospective primers, not only for this particular example but also for other examples of this disclosure.

EXAMPLE 3

The PCR Assay

The PCR was performed from human genomic DNA isolated from white blood cells, although DNA from other cells could also be used. Unless otherwise stated, the PCR mixtures contained a total volume of 25 μL: 50 mM Tris-HCl, pH 9.2, 2.25 mM $MgCl_2$, 16 mM $(NH_4)_2SO_4$, 7.5% DMSO, 500 μM of dGTP and deaza-dGTP (62.5%:37.5% or 50%:50%), 500 μM of each of the other dNTPs, 250 ng of genomic DNA.

Three types of cycling conditions were utilized: three-temperature PCR, two-temperature PCR and S-PCR. The cycling conditions for three-temperature PCR were 94° C. for 12 seconds, 65° C. for 30 seconds and 68° C. for 14 minutes for the first 10 cycles (Perkin Elmer GeneAmp PCR System 9600). The remaining 20 cycles were performed by adding an extra 20 seconds to the elongation per cycle.

Conditions for two temperature cycling were: 94° C. for 12 seconds and 65° C. for 15 minutes for the first 10 cycles, with an extra 20 seconds added to the elongation per cycle for the remaining 20 cycles.

The conditions for S-PCR for the first 10 cycles were: 94° C. for 12 seconds, followed by four subcycles of annealing/elongation that involve 60° C. for 120 seconds and 65° C. for 120 seconds for each subcycle. The remaining 20 cycles were modified by the addition of an extra three seconds per cycle for each step of the annealing/elongation step.

An additional two minutes of denaturation was utilized at the start in the first cycle for each of the 3 types of cycling. The optimal enzyme amount and primer concentration depended on the types of cycling conditions. For Expand™ Long Template DNA polymerase, amounts of enzyme (total of Taq and Pwo) and primers (P, Q, A and B) are as follows:

i) for three-temperature cycling: 3.3 U and 0.4 μM, 0.4 μM, 0.12 μM and 0.12 μM;

ii) for two-temperature cycling: 2.5 U and 0.2 μM, 0.2 μM, 0.15 μM and 0.15 μM; and iii) for S-PCR: 2.5 U and 0.2 μM, 0.2 μM, 0.2 μM and 0.2 μM.

Ten μL of the reaction was mixed with an equal amount of 2×loading buffer (5% Ficoll 400, 5 mM $MgCl_2$, 25 mM NaCl, 10 mM TrisHCl, pH 7.9) and then incubated at 37° C. for 5 minutes. Samples were electrophoresed on a 0.6% agarose gel, and then stained with ethidium bromide for UV photography by a CCD camera (Bio-Rad Gel Doc 1000).

EXAMPLE 4

Effects of DMSO, Deaza-dGTP and Enzyme Concentration on PCR Products

Figure 5A:
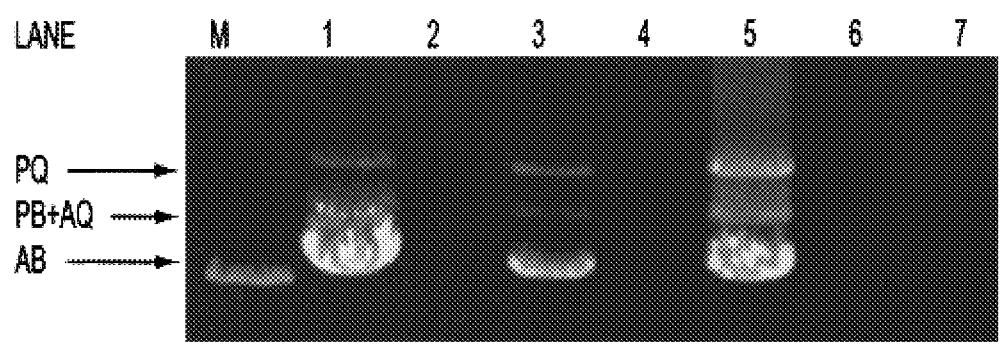
FIG. 5A shows the effects of DMSO and deaza-dGTP. 0.2 $\mu$M each of primers P, Q, A and B were used to amplify the carrier DNA template. Lanes 1–2: standard three-temperature cycling conditions for long distance PCR (94° C., 65° C. and 68° C.); lanes 3–4: three-temperature cycling conditions but the annealing temperature is lowered from 65° C. to 60° C.; lanes 5–7: two-temperature PCR (94° C. and 65° C.). The samples in the first of each pair of lanes were amplified with optimal components of DMSO (7.5%), deaza-dGTP (37.5%) and Taq/Pwo (2.5 units per 25 $\mu$L reaction). In lanes 2 and 4, the maximum concentration of DMSO recommended by Boehringer Mannheim (2%), no deaza-dGTP and the maximum enzyme concentration recommended by Boehringer Mannheim (1.2 units). In lanes 6 and 7, amplification was performed as in lane 5, except with 2% DMSO (lane 6) or the absence of deaza-dGTP (lane 7). M is a size marker of 9.4 kb.
Figure 5B:
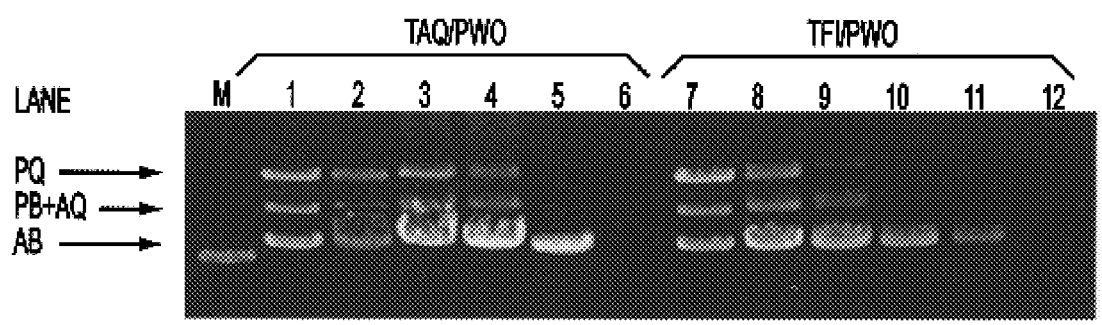
FIG. 5B shows the effect of enzyme concentration. Lanes 1–6 contain, respectively, 10 U, 5 U, 2.5 U, 1.25 U, 0.62 U and 0.31 U of Taq/Pwo (total of the two enzymes using the Expand™ Long Template PCR System (Boehringer Mannheim)) per 25 $\mu$L reaction; lanes 7–12 contain Tfl/Pwo at a ratio of 30 units: 1 unit, with 10, 5, 2.5, 1.25, 0.62 and 0.31 units of Tfl used in the reaction shown in lanes 7–12, respectively. Two-temperature PCR was performed with 7.5% DMSO and 37.5% deaza-dGTP. M=size standard, only the 9.4 kb fragment is shown (200 ng of $\lambda$ DNA/HindIII).

Successful amplification required 6–9% DMSO, 25–50% deaza-dGTP (as a percentage of the dGTP concentration), and 1.25–10 U enzymes with optimal results achieved at 5–10 U per 25 μL reaction. The effects of varying these parameters using the two-temperature PCR conditions are shown in FIGS. 5A and 5B and in Table 2.

EXAMPLE 5

Effect of Different DNA Polymerase Combinations on PCR Products

Analysis of several DNA polymerase systems other than the Expand™ Long Template DNA polymerase system was performed. The other systems tested include Taq/Vent (Boehringer Mannheim/New England BioLabs), ELON-Gase™ Enzyme system which contains Taq/GB-D DNA polymerases (Life Technologies), Tth/Pwo (Boehringer Mannheim), Tth/Vent, Tfl/Pwo (Promega/Boehringer Mannheim), Tfl/Vent, and Bio-X-ACT™ DNA polymerase (Intermountain Scientific). The results using the two-temperature cycling conditions are shown in FIG. 5B and Table 3. These results indicate that high concentrations of DMSO and deaza-dGTP are critical for all enzymes studied, while high enzyme concentration was helpful, but not universally critical.

EXAMPLE 6

PCR Subcycling Assays

Figure 6:
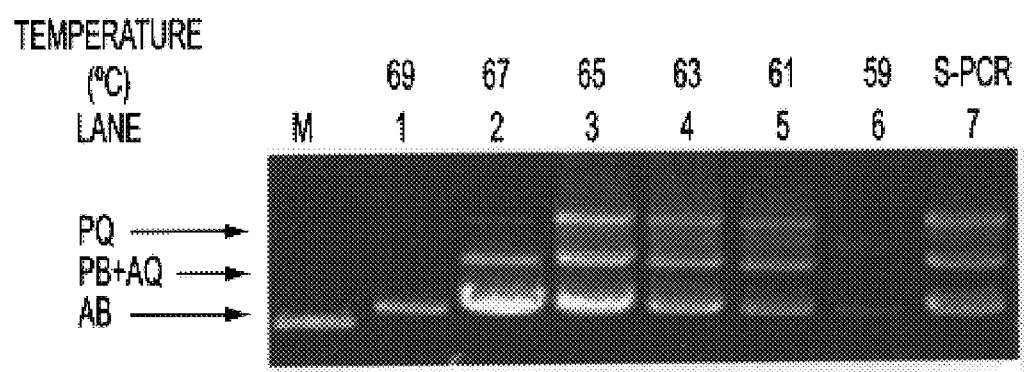
FIG. 6 shows the effect of annealing/elongation temperature and S-PCR. Primers P, Q, A and B were used to amplify the carrier DNA template with each primer at 0.2 μM concentration. Two-temperature cycling was used with annealing/elongation temperatures varying from 69–59° C. PCR was performed with a temperature gradient Robocycler (Stratagene) with slightly modified periods of denaturation and annealing/elongation designed to be equivalent to amplification of the PE GeneAmp 9600 thermal cycler based on the manufacturer's protocol. In lane 7, S-PCR was performed for comparison. M is a size marker of 9.4 kb.

Despite substantial efforts at optimization, segment AB was amplified much more efficiently than segments PQ, PB or AQ with standard three-temperature cycling (shown in Lane 1 of FIG. 5A). Preferential amplification is often a problem in multiplex PCR, especially if segments with divergent GC contents are amplified. Although even one nucleotide change in a sequence sometimes causes differential amplification (Liu et al., 1997b), we reasoned that areas of low GC content in the 2.5 kb of the flanking sequences present in segment PQ could account for some or all of the differential efficiency of amplification. Since the optimal extension temperature varies with GC content (Su et al., 1996), the annealing/elongation temperature was lowered. Much of the differential amplification was eliminated, but the yields of amplified product were both lowered and inconsistent with a faint spurious band (FIG. 6, lanes 1–6). In

TABLE 2

The Key Component Parameters

| Component changed[a] | | Amplifications |
| --- | --- | --- |
| DMSO (%) | 10.5 | –[c] |
| | 9 | ++ |
| | 7.5 | +++ |
| | 6 | ++ |
| | 4.5 | – |
| | 0 | – |
| deaza-dGTP:dGTP (%:%) | 50:50 | +++/++ (AB/PQ)[b] |
| | 37.5:62.5 | +++/+++ |
| | 25:75 | ++/++ |
| | 0:100 | –/– |
| Taq/Pwo (U/25 μL) | 10 | +++/+++ (AB/PQ) |
| | 5 | +++/+++ |
| | 2.5 | +++/++ |
| | 1.25 | +++/+ |
| | 0.625 | ++/– |
| | 0.3125 | –/– |
| | 0 | –/– |

[a]Only one component was changed. The effect was tested with the four primers (each at 0.2 μM) at 65° C. for the annealing/elongation.
[b]AB and PQ segments are indicated in order.
[c]The yield of the PCR product is indicated as: –, no DNA band on the agarose gel stained by ethidium bromide for UV photography; ±, very weak DNA band; +, weak DNA band; ++, strong DNA band, +++, very strong DNA band.

TABLE 3

Comparison of Different Enzyme Systems

| DNA Polymerases[a] | Optimal para-meters[b] (I + II+III) | Single parameter changed[c] | | | Standard con-ditions[d] (–I–II–III) |
| --- | --- | --- | --- | --- | --- |
| | | 2% DMSO (–I) | Only dGTP | Standard enzymes (–III) | |
| Taq/Pwo | +++/++[e] (AB/PQ) | –/– (AB/PQ) | –/– (AB/PQ) | +++/+ (AB/PQ) | –/– (AB/PQ) |
| Taq/Vent | +++/++ | –/– | –/– | +++/+ | –/– |
| ELONGase™ | +++/++ | –/– | –/– | ++/± | –/– |
| Tth/Pwo | –/– | –/– | –/– | –/– | –/– |
| Tth/Vent | –/– | –/– | –/– | –/– | –/– |
| Tfl/Pwo | ++/+ | –/– | –/– | ++/– | –/– |
| Tfl/Vent | ++/+ | –/– | –/– | –/– | –/– |
| Bio-X-ACT™ | –/– | –/– | –/– | –/– | –/– |

Figure 3B:
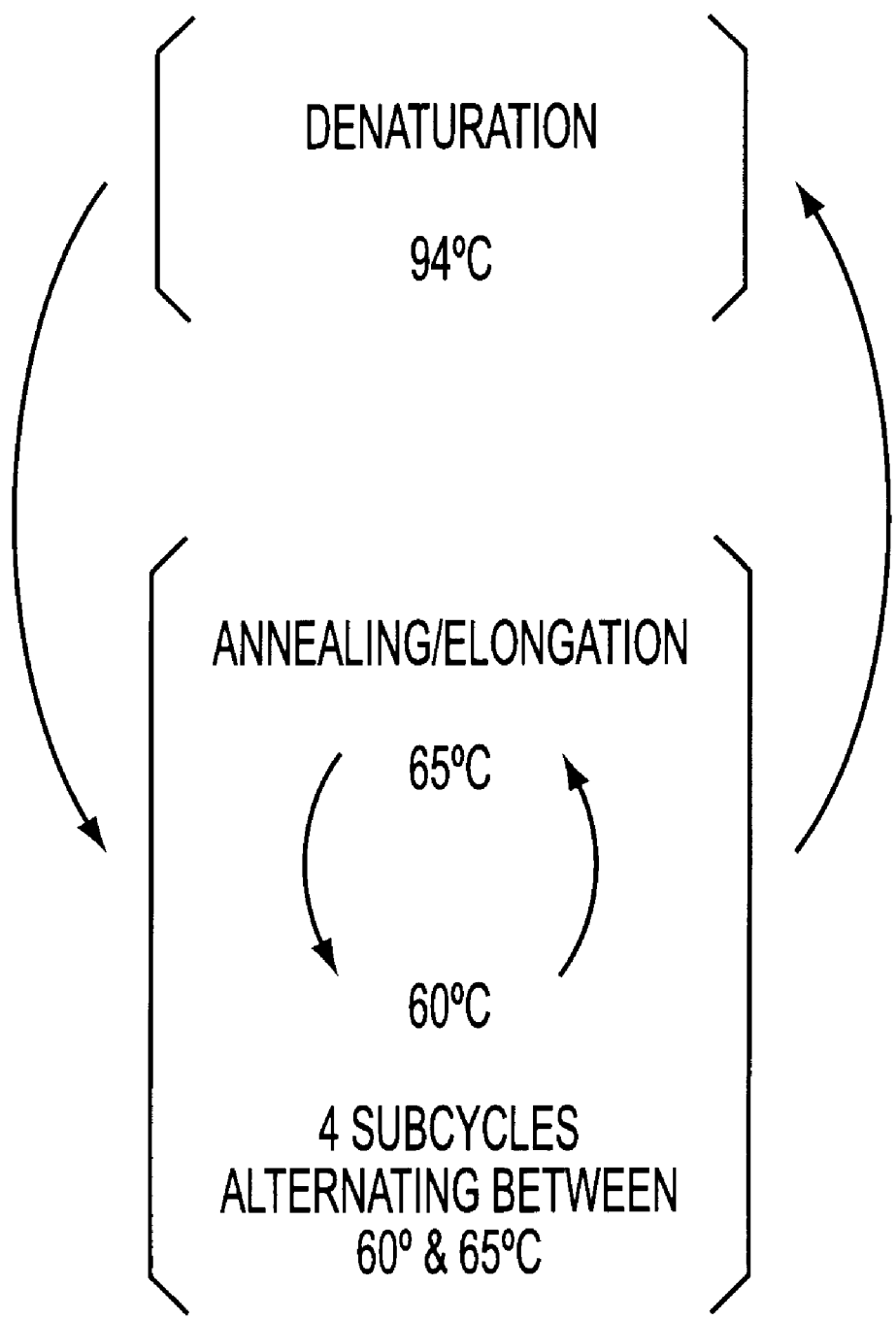
FIG. 3B shows a schematic of subcycling-PCR. Each cycle of S-PCR involves a denaturation step and an annealing/elongation step. The annealing/elongation step is composed of subcycles to shuttle among low and high temperatures.

[a]The ratios of Taq/Vent, Tth/Pwo, Tth/Vent, Tfl/Pwo, Tfl/Vent were 30:1 (U:U). The segments were amplified from the carrier DNA with four primers (each 0.2 μM) at 65° C. for extension. AB and PQ segments are indicated in order.
[b]Optimal parameters: I = 7.5% DMSO, II = 37.5 deaza-dGTP and III = 2.5 U of enzymes.
[c]One of the parameters was changed, assigned as –I, –II and –III. Low enzyme = 1.2 U.
[d]Standard conditions = 2% DMSO and dGTP, 1.2 U of enzymes per 25 μL reaction.
[e]The yield of the PCR product is indicated as: –, no DNA band on the agarose gel stained by ethidium bromide for UV photography; ±, very weak DNA band; +weak DNA band; ++, strong DNA band; +++very strong DNA band.

order to obtain high and relatively uniform yields, we developed subcycling PCR (S-PCR), which is characterized by "subcycling parameters" within the annealing/elongation step (FIG. 3B). With the subcycling parameters between 60° C. and 65° C., S-PCR amplified the four segments more evenly and efficiently with the four primers from the carrier DNA template (lane 7 in FIG. 6). When the wildtype and inversion templates were used, the same results were obtained. Similar results were obtained with a four-step subcycling program: two subcycles at 60° C., 64° C., 68° C., 64° C. for two minutes each for a total of 16 minutes (data not shown).

In Example 3 discussed above, the subcycling temperatures were held at 60° C. and 65° C. for 120 seconds for each subcycle, but subcycling in general need not include holding the temperature at a single temperature for an extended time. Instead the subcycling can be continuous with the temperature being ramped up to, e.g., 65° C., immediately ramped down to the lower temperature, e.g., 60° C., and then again immediately ramped up to 65° C., etc.

If the number of shuttled temperatures within a subcycle is referred to as "m" and the number of subcycles is referred to as "n", then by definition subcycling PCR requires that m is $\geq 2$, n is $\geq 1$, and $(m) \times (n) \geq 3$.

Figure 7:
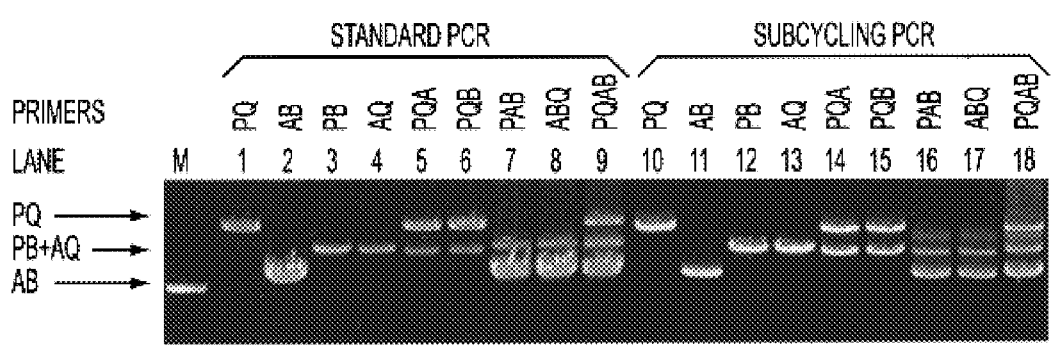
FIG. 7 shows the interaction among the primers. Two-, three- and four-primers were utilized to amplify the carrier template. Standard three-temperature PCR was used in lanes 1 to 9. Concentrations of the four primers were 0.4, 0.4, 0.12 and 0.12 μM, respectively, for P, Q, A and B. S-PCR was used in lanes 10 to 18 and each primer concentration was 0.2 μM.

To compare standard three-temperature PCR with S-PCR, combinations of two, three and four primers were tested on the carrier templates. For standard PCR, virtually none of segments PQ, PB or AQ was amplified in carriers (estimated molar ratios of more than 20:1), when the molar ratios of the primers were equal. Multiple optimization experiments were undertaken, resulting in primer concentrations of 0.4 μM for primers P and Q, and 0.12 μM for primers A and B. These optimized primer concentrations were compared with S-PCR utilizing equal molar ratios of 0.2 μM (FIG. 7). The relative yields with three primers in the lanes 4 to 8 were the most uneven with four-fold differences among the products, in comparison with two-fold differences in lanes 14 to 18. Similar tendencies were observed when wildtype and inversion genomic DNAs were used (data not shown). The results with two-temperature cycling were between three-temperature PCR and S-PCR (data not shown). It is to be noted that the PCR assays performed with only 3 primers rather than all 4 primers were able to differentiate the wildtype, inversion and carrier in a single reaction (FIG. 7 and data not shown) and use of only 3 primers is an alternative method to using 4 primers. It is also noted that other alternative methods of PCR assays with each two primer pair in two to four reactions were able to differentiate the wildtype, inversion and carrier (FIG. 7 and data not shown).

We have seen that the optimal primer concentrations depend on the cycling conditions. For the three-temperature PCR with elongation temperature at 68° C., the optimal concentrations are 0.4, 0.4, 0.12 and 0.12 $\mu$M for P, Q, A and B, respectively. For two-temperature PCR with annealing/elongation at 65° C. the optimal primer concentrations are 0.2, 0.2, 0.15 and 0.15 $\mu$M for P, Q, A and B, respectively. For subcycling-PCR (as outlined above) the optimal primer concentrations are 0.2 $\mu$M for each of the primers.

Subcycling PCR can also be applied other variations of PCR, e.g.,to random PCR, i.e., to PCR in which random primers are being utilized. The Examples are not meant to be limiting in the use of subcycling PCR, the subcycling step being applicable to any method of PCR.

EXAMPLE 7

Effect of Primer Concentrations on Multiplex PCR

Figure 8A:
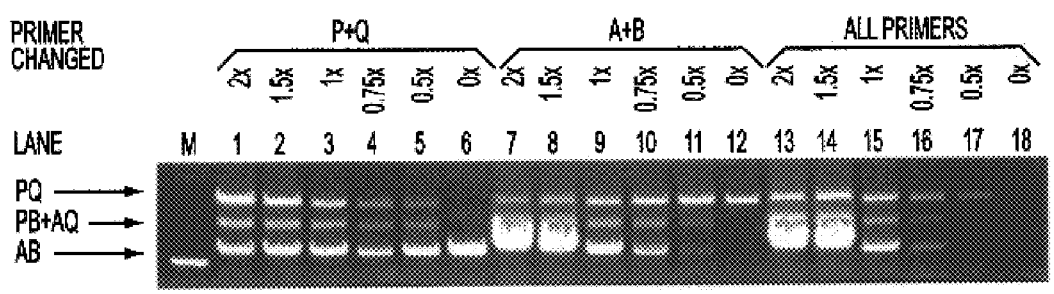
FIGS. 8A and 8B show the effect of primer concentration. Carrier DNA template was used for all of the reactions. Lanes 1–6, 7–12 and 13–18 show the effect of varying only the P and Q primers, only A and B primers, and all four primers, respectively.
Figure 8B:
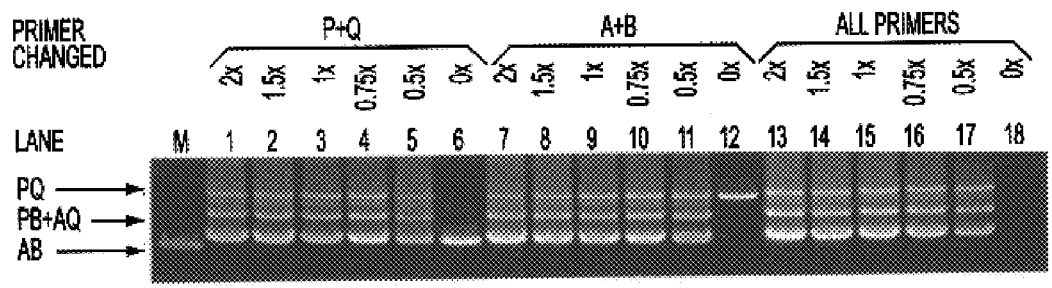

FIGS. 8A and 8B show the effects on the relative yields when the concentrations of only primers P and Q (lanes 1–6), of only primers A and B (lanes 7–12), or of all the four primers (lanes 13–18) were varied with carrier DNA as template. Small changes in the primer concentration caused dramatic effects on the relative yields of segments PQ, AB, and PB+AQ with three-temperature PCR (FIG. 8A), but not with S-PCR (FIG. 8B). Two-temperature cycling gave results between three-temperature PCR and S-PCR (data not shown).

The preceding Examples have illustrated a technique of combining long distance PCR with multiplex PCR with modifications, some of which are optional such as use of S-PCR, as applied to the study of a common chromosomal inversion. These same methods are also applicable to any other known inversion and the methods are further applicable to the analysis of other chromosomal aberrations such as deletions/inversions and translocations. To perform such analyses, the specific chromosomal aberration and some DNA sequence in the vicinity of the aberration must be known so that appropriate primers may be prepared. This will be especially useful for commonly occurring chromosomal aberrations such as the factor VIII inversion or for analyses of family members once a chromosomal aberration has been found and analyzed in a first family member by other means and it is then desired to screen blood relatives of this first family member by a simple technique such as PCR. PCR reactions can be performed as described above and any variation of the method can be utilized, e.g., one can use two temperature cycling, three temperature cycling or subcycling PCR, and one can use three primers, four primers or more than four primers for multiplex PCR. The primers can be selected such that different sizes of PCR products will result when the assay is performed on a person who is wild-type compared to the results seen when the assay is performed on a person who has the chromosomal aberration, this method allowing for easy diagnosis by using gel electrophoresis to examine the size products which are formed. Nevertheless, it is not necessary to select primers to yield different sized PCR products since it is possible to determine which products are produced by means other than size of the products, e.g., hybridization techniques may be used. Preferred methods will also use high levels of DMSO and DNA polymerase and will also incorporate the use of deaza-dGTP. The described methods are especially useful for the analysis of gross aberrations such as inversions, large deletions/inversions and translocations but they are also applicable to smaller mutations.

Some chromosomal mutations, such as inversions, deletions/inversions (where an inversion and a deletion occur concomitantly), and translocations have similar structural characteristics to the inversion in the factor VIII gene. A crossover recombination occurs between two regions which are located on one or two chromosomes, resulting in new alleles. The two regions may be homologous or non-homologous. Also, one allele may contain two or more copies. In such cases, this approach can be used.

P and Q are sequence-specific to a first allele in flanking regions of the recombination region, and A and B are sequence-specific to a second allele in flanking regions of the recombination region. Any chromosomal mutation may occur between the first and second alleles which results in two new alleles, i.e., a third and a fourth allele, represented by PB and AQ (balance) or which result in PB and/or AQ (unbalance). DNA which is homozygous wildtype for the first two alleles results in amplification of the two segments PQ and AB. DNA which is homozygous with the mutation with respect to the third and fourth alleles results in amplification of PB and/or AQ segments. DNA which is heterozygous with respect to the 4 alleles results in amplification of PQ, AB, PB and/or AQ. Also, if one allele is present in two or more copies, the intact allele is always amplified.

Inversions resulting from homologous recombination between a gene and a homolog of the gene, can also be tested exactly as was done for the factor VIII gene inversion, except that it may often be the case that only a single homologous region is present in the genome and not two homologous regions as is the case for intron 22 of the factor VIII gene. With only one gene and a single homologous region being present, when an inversion occurs only the size products resulting from the inversion will be seen, there will not be any wild-type size products present as in the case of the factor VIII gene which always had one wild-type product present because only one of the two homologs of Int22h1 could be involved in the inversion. At least some of the primers are selected from flanking regions which are specific for either the gene or for its homolog thereby allowing one to distinguish between the gene, the homolog and an inversion resulting from a recombination between the gene and its homolog. The primers can be chosen to yield different sized products in order to allow for a simple determination of the genotype of the sample being assayed, but it is also possible to use primers which yield products of the same size and which are differentiated by means other than size, e.g., by hybridization techniques or restriction enzyme analysis.

In a similar fashion, translocations involving two chromosomes can be detected by using long distance, multiplex PCR. The translocation will involve a breakpoint in each of two chromosomes. Primers are used from each side of each chromosome spaced so as to yield different sized PCR products depending upon whether the product results from the first wild-type chromosome, the second wild-type chromosome, or a first product from a translocation or a second product from a translocation. The presence and/or absence of the various sized products indicates the presence or absence of a translocation. It is possible to use simply two primers wherein one primer is upstream of one breakpoint and the second primer is downstream from the other breakpoint. The presence of a product using these two primers-is indicative of translocation having occurred. Multiplex PCR will be performed with more than 2 primers, and can involve 3, 4 or more primers. The long distance PCR utilizes primers far enough from the breakpoints such that at least one product at least 4 kb in length is produced. Use of long distance PCR allows for using primers farther apart and therefore allows for some leeway as to the exact location of the translocation. The same is true concerning use of these methods to assay for inversions or deletions/inversions wherein the exact point or size of the inversion or deletion/inversion may not be known ahead of time.

Although the methods have been demonstrated by measuring the size of PCR products via agarose gel electrophoresis, the claims are not meant to be limited to use of such a technique. Those of skill in the art know various techniques of measuring the sizes of PCR products. It is further envisioned that the PCR products may be subjected to restriction endonuclease cleavage prior to having their lengths measured.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Antonarakis S E, Rossiter J P, Young M, Horst J, de Moerloose P, Sommer S S, Ketterling R P, Kazazian H H, Négrier C, Vinciguerra C, Gitschier J, Goossens M, Girodon E, Ghanem N, Plassa F, Lavergne J M, Vidaud M, Costa J M, Laurian Y, Lin S-W, Lin S-R, Shen M-C, Lillicrap D, Taylor S A M, Windsor S, Valleix S V, Nafa K, Sultan Y, Delpech M, Vnencak-Jones C L, Phillips J A, Ljung R C R, Koumbarelis E, Gialeraki A, Mandalaki T, Jenkins P V, Collins P W, Pasi K J, Goodeve A, Peake I, Preston F E, Schwartz M, Scheibel E, Ingerslev J, Cooper D N, Millar D S, Kakkar V V, Giannelli F, Naylor J A, Tizzano E F, Baiget M, Domenech M, Altisent C, Tusell J, Beneyto M, Lorenzo J I, Gaucher C, Mazurier C, Peerlinck K, Matthijs G, Cassiman J J, Vermylen J, Mori P G, Acquila M, Caprino D and Inaba H (1995). *Blood* 86:2206–2212.

Barnes W M (1994). *Proc. Natl. Acad. Sci. USA* 91:2216–2220.

Baskaran N, Kandpal R P, Bhargava A K, Glynn M W, Bale A and Weissman S M (1996). *Genome Research* 6:633–638.

Breslauer K J, Frank R, Blocker H and Markey L A (1986). *Proc. Natl. Acad Sci. U.S.A.* 83:3746–3750.

Chamberlain J S, Gibbs R A, Ranier J E, Nguyen P N and Caskey C T (1998). *Nucleic Acids Research* 16:11141–11156.

Cheng S, Fockler C, Barnes W M and Higuchi R (1994). *Proc. Natl Acad Sci. USA* 91:5695–5699.

Freier S M, Kierzek R, Jaeger J A, Sugimoto N, Caruthers M N, Neilson T and Turner D H (1986). *Proc. Natl. Acad. Sci. U.S.A.* 83:9373–9377.

Henegariu O, Heerema N A, Dlouhy S R, Vance G H and Vogt P H (1997). *BioTechniques* 23:504–511.

Lakich D, Kazazian H H, Antonarakis S E and Gitschier J (1993). *Nature Genet.* 5:236–241.

Liu Q, Thorland E C, Heit J A and Sommer S S (1997a). *Genome Research* 7:389–398.

Liu Q, Thorland E C and Sommer S S (1997b). *BioTechniques* 22:292–300.

Naylor J, Brinke A, Hassock S, Green P M and Giannelli F (1993). *Hum. Molec. Genet.* 2:1773–1778.

Naylor J A, Buck D, Green P, Williamson H, Bentley D and Giannelli F (1995). *Hum. Molec. Genet.* 4:1217–1224.

Ochman H, Gerber A S and Hartl D L (1988). *Genetics* 120:621–623.

Shuber A P, Grondin V J and Klinger K W (1995). *Genome Research* 5:488–493.

Su X, Wu Y, Sifri C D and Wellems T E (1996). *Nucleic Acids Research* 24:1574–1575.

Wetmur J G (1991). *Criti. Rev. Biochem. Mol. Biol.* 26:227–259.

What is claimed is:

1. A method for screening for the presence of hemophilia A in a male wherein said method comprises performing long distance polymerase chain reaction (PCR) on a sample from said male using 2 primers, wherein said primers are specific for amplifying a region of an X chromosome comprising intron 22 of a factor VIII gene (Int22h1), wherein said method is performed under conditions which produce a PCR product when performed on a sample from a person who does not have hemophilia A, wherein the absence of a PCR product indicates the presence of hemophilia A in said male.

2. The method of claim 1 wherein one of said primers comprises SEQ ID NO:8 and another of said primers comprises SEQ ID NO:9.

3. A method for determining the presence of hemophilia A in a male or the presence in a female of an inversion comprising intron 22 of a factor VIII gene wherein said inversion results from a homologous recombination between Int22h1 and Int22h2 or Int22h3 and wherein said inversion results in hemophilia A when a person is hemizygous or homozygous for said inversion, wherein said method comprises performing long distance polymerase chain reaction on a sample from said male or said female using 2 primers, wherein a) a first primer is specific for a region upstream of Int22h1 and a second primer is specific for a region downstream of both Int22h2 and Int22h3 or b) a first primer is specific for a region upstream of both Int22h2 and Int22h3 and a second primer is specific for a region downstream of Int22h1, wherein the presence of a PCR product is indicative of hemophilia A in said male and is indicative of said female being a carrier of said inversion.

4. The method of claim 3 wherein said primers are selected from primers comprising a) SEQ ID NO:8 and SEQ ID NO:11, b) SEQ ID NO:8 and bases 1–36 of SEQ ID NO:11, or c) SEQ ID NO:10 and SEQ ID NO:9.

5. A method for screening for the presence of hemophilia A in a male or the absence of an inversion in either a male or the presence of said inversion in a female, wherein said inversion results from a homologous recombination between Int22h1 and Int22h2 or Int22h3 and wherein said inversion causes hemophilia A when present in a male, wherein said method comprises performing long distance, multiplex PCR on a sample from said male or from said female using 3 primers wherein a first primer is specific for an upstream region of Int22h1, a second primer is specific for a downstream region of Int22h1, and a third primer is specific for either an upstream or a downstream region of both Int22h2 and Int22h3, wherein amplification using said first primer and said second primer yields a PCR product of a first size and wherein amplification using said third primer and one of said second primer and said third primer yields a PCR product of a second size, wherein the presence of a PCR product of said first size is indicative that said male does not carry said inversion and wherein the presence of a PCR product of said second size is indicative that said male has hemophilia A or that said female is a carrier of said inversion.

6. The method of claim 5 wherein said first primer comprises SEQ ID NO:8, b) said second primer comprises SEQ ID NO:9 and c) said third primer is selected from the group consisting of a primer comprising SEQ ID NO:10, a primer comprising SEQ ID NO:11 and a primer comprising bases 1–36 of SEQ ID NO:11.

7. A method for screening for the presence of hemophilia A in a male or the absence of an inversion in a male or the presence of said inversion in a female, wherein said inversion results from a homologous recombination between Int22h1 and Int22h2 or Int22h3 and wherein said inversion causes hemophilia A when present in a male, wherein said method comprises performing long distance, multiplex PCR on a sample from said male or from said female using 3 primers wherein a first primer is specific for both an upstream region of Int22h2 and an upstream region of Int22h3, a second primer is specific for both a downstream region of Int22h2 and a downstream region of Int22h3, and a third primer is specific for either an upstream or a downstream region of Int22h1, wherein amplification using said first primer and said second primer yields a PCR product of a first size and wherein amplification using said third primer and one of said first primer and said second primer yields a PCR product of a second size, wherein the presence of a PCR product of said second size in a sample from said male is indicative of the presence of hemophilia A in said male, the absence of a PCR product of said second size in a sample from said male is indicative of the absence of said inversion in said male, the presence of a PCR product of said second size in a sample from said female is indicative that said female is a carrier of said inversion, and the absence of a PCR product of said second size in a sample from said female is indicative that said female is not a carrier of said inversion.

8. The method of claim 7 wherein said first primer comprises SEQ ID NO:10, b) said second primer comprises SEQ ID NO:11 or bases 1–36 of SEQ ID NO:11, and c) said third primer comprises SEQ ID NO:8 or SEQ ID NO:9.

9. A method for screening for the presence of hemophilia A in a male or the absence of an inversion in a male, wherein said inversion results from a homologous recombination between Int22h1 and Int22h2 or Int22h3 and wherein said inversion causes hemophilia A when present in a male, or to determine whether a female is a carrier of said inversion, wherein said method comprises performing long distance, multiplex PCR on a sample from said male or from said female using 4 or more primers wherein a first primer is specific for an upstream region of Int22h1, a second primer is specific for a downstream region of Int22h1, a third primer is specific for an upstream region of both Int22h2 and Int22h3, and a fourth primer is specific for a downstream region of both Int22h2 and Int22h3, wherein a PCR amplification product using said first primer and said second primer is a first size, a PCR amplification product using said third primer and said fourth primer is a second size, a PCR amplification product using said first primer and said fourth primer is a third size and a PCR amplification product using said second primer and said third primer is a fourth size, wherein said first size and said second size may be equal to each other and wherein said third size and said fourth size may be equal to each other, wherein the presence of PCR amplification products of said first size and said second size in a sample from a male indicates the absence of said inversion in said male, the presence of PCR amplification products of said second size, said third size and said fourth size in a sample from a male indicates the presence of hemophilia A in said male, the presence of PCR amplification products of said first size and said second size and the absence of PCR amplification products of said third size and said fourth size in a sample from a female indicates the absence of said inversion in said female, and the presence of PCR amplification products of said first size, said second size, said third size and said fourth size from a sample from said female indicates that said female is a carrier of said inversion.

10. The method of claim 9 wherein said first primer comprises SEQ ID NO:8, b) said second primer comprises SEQ ID NO:9, c) said third primer comprises SEQ ID NO:10, and d) said fourth primer comprises SEQ ID NO:11 or bases 1–36 of SEQ ID NO:11.

11. The method of claim 1 wherein said PCR comprises any combination of one, two or three of the following:
   i) DMSO at a concentration of at least 6%;
   ii) DNA polymerase at a concentration of at least 0.05 units per µL; and
   iii) a concentration of deaza-dGTP and a concentration of dGTP wherein said concentration of deaza-dGTP is greater than or equal to 33% of said concentration of dGTP.

12. The method of claim 3 wherein said PCR comprises any combination of one, two or three of the following:
   i) DMSO at a concentration of at least 6%;
   ii) DNA polymerase at a concentration of at least 0.05 units per µL; and
   iii) a concentration of deaza-dGTP and a concentration of dGTP wherein said concentration of deaza-dGTP is greater than or equal to 33% of said concentration of dGTP.

13. The method of claim 5 wherein said PCR comprises any combination of one, two or three of the following:
   i) DMSO at a concentration of at least 6%;
   ii) DNA polymerase at a concentration of at least 0.05 units per µL; and
   iii) a concentration of deaza-dGTP and a concentration of dGTP wherein said concentration of deaza-dGTP is greater than or equal to 33% of said concentration of dGTP.

14. The method of claim 7 wherein said PCR comprises any combination of one, two or three of the following:
   i) DMSO at a concentration of at least 6%;
   ii) DNA polymerase at a concentration of at least 0.05 units per µL; and
   iii) a concentration of deaza-dGTP and a concentration of dGTP wherein said concentration of deaza-dGTP is greater than or equal to 33% of said concentration of dGTP.

15. The method of claim 9 wherein said PCR comprises any combination of one, two or three of the following:
   i) DMSO at a concentration of at least 6%;
   ii) DNA polymerase at a concentration of at least 0.05 units per µL; and
   iii) a concentration of deaza-dGTP and a concentration of dGTP wherein said concentration of deaza-dGTP is greater than or equal to 33% of said concentration of dGTP.

16. The method of claim 1 wherein
   i) said PCR comprises two temperatures,
   ii) said PCR comprises three temperatures, or
   iii) said PCR comprises subcycling PCR.

17. The method of claim 3 wherein
   i) said PCR comprises two temperatures,
   ii) said PCR comprises three temperatures, or
   iii) said PCR comprises subcycling PCR.

18. The method of claim 5 wherein
   i) said PCR comprises two temperatures,
   ii) said PCR comprises three temperatures, or
   iii) said PCR comprises subcycling PCR.

19. The method of claim 7 wherein
   i) said PCR comprises two temperatures,
   ii) said PCR comprises three temperatures, or
   iii) said PCR comprises subcycling PCR.

20. The method of claim 9 wherein
   i) said PCR comprises two temperatures,
   ii) said PCR comprises three temperatures, or
   iii) said PCR comprises subcycling PCR.

21. The method of claim 5 wherein said PCR is performed in a single reaction vessel.

22. The method of claim 7 wherein said PCR is performed in a single reaction vessel.

23. The method of claim 9 wherein said PCR is performed in a single reaction vessel.

24. A nucleic acid comprising at least 13 consecutive bases of a DNA sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and bases 1–36 of SEQ ID NO:11.

25. A nucleic acid of claim 24 wherein said DNA sequence is selected from the group consisting of SEQ ID NO:1, SEQ ID NO:2, SEQ ID NO:4 and SEQ ID NO:5.

26. A nucleic acid of claim 24 wherein said DNA sequence is selected from the group consisting of SEQ ID NO:3, SEQ ID NO:6 and SEQ ID NO:7.

27. A nucleic acid of claim 26 wherein said DNA sequence is selected from the group consisting of SEQ ID NO:8, SEQ ID NO:9, SEQ ID NO:10, SEQ ID NO:11 and bases 1–36 of SEQ ID NO:11.

28. A nucleic acid consisting of a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and bases 1–36 of SEQ ID NO:11.

* * * * *

UNITED STATES PATENT AND TRADEMARK OFFICE
CERTIFICATE OF CORRECTION

PATENT NO. : 6,355,422 B1
DATED : March 12, 2002
INVENTOR(S) : Qiang Liu et al.

It is certified that error appears in the above-identified patent and that said Letters Patent is hereby corrected as shown below:

Column 10,
Line 37, "Int22h1." should be -- Int22h1, --;

Column 26,
Line 58, "26" should be -- 24 --.

Signed and Sealed this

Twenty-eighth Day of September, 2004

JON W. DUDAS
*Director of the United States Patent and Trademark Office*